US009316642B2

(12) United States Patent
Faatz et al.

(10) Patent No.: US 9,316,642 B2
(45) Date of Patent: Apr. 19, 2016

(54) SOLUBLE IMMUNOREACTIVE TREPONEMA PALLIDUM TPN47 ANTIGENS

(71) Applicant: Roche Diagnostics Operations, Inc., Indianapolis, IN (US)

(72) Inventors: Elke Faatz, Huglfing (DE); Peter Schaarschmidt, Ulm (DE); Urban Schmitt, Kochel (DE); Christian Scholz, Penzberg (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 14/335,022

(22) Filed: Jul. 18, 2014

(65) Prior Publication Data

US 2015/0079604 A1 Mar. 19, 2015

Related U.S. Application Data

(63) Continuation of application No. PCT/EP2013/000108, filed on Jan. 16, 2013.

(51) Int. Cl.

*A61K 39/02* (2006.01)
*A61K 39/00* (2006.01)
*G01N 33/53* (2006.01)
*G01N 33/571* (2006.01)
*C07K 14/20* (2006.01)

(52) U.S. Cl.

CPC .............. *G01N 33/571* (2013.01); *C07K 14/20* (2013.01); *C07K 2319/00* (2013.01); *G01N 2333/20* (2013.01); *G01N 2469/20* (2013.01)

(58) Field of Classification Search

CPC ..... A61K 38/00; A61K 38/16; A61K 38/164; A61K 39/02; A61K 9/0225

See application file for complete search history.

(56) References Cited

FOREIGN PATENT DOCUMENTS

CN 101293919 A 10/2008

OTHER PUBLICATIONS

International Search Report issued Apr. 3, 2013, in Application No. PCT/EP2013/000108, 5 pages.

Baughn, Robert E. et al., “Molecular Mimicry Between an Immunodominant Amino Acid Motif on the 47-kDa Lipoprotein of Treponema pallidum (Tpp47) and Multiple Repeats of Analogous Sequences in Fibronectin,” The Journal of Immunology, 1996, pp. 720-731, vol. 157.

Deka, Ranjit K. et al., “Crystal Structure of the 47-kDa Lipoprotein of Treponema pallidum Reveals a Novel Penicillin-binding Protein,” The Journal of Biological Chemistry, 2002, pp. 41857-41864, vol. 277, No. 44.

Guo, Qing-Shun et al.,“Expression of Treponema pallidum 47 ku Fragments and Analysis of Its Epitope,” 2008, pp. 874-878, vol. 47, No. 6.

Rostopira, N. et al., “Elaboration of Enzyme Immunoassay Based on Recombinant Antigens and intended for Diagnostics of Syphilis,” Folia Microbiology, 2003, pp. 549-553. vol. 48, No. 4.

Tomchick, Diana R. et al., “Tp47: A New Structural Paradigm for Penicillin-Binding Proteins,” FASEB Journal Experimental Biology 2002: Meeting Abstracts, p. A136, vol. 16, No. 4.

*Primary Examiner* — Rodney P Swartz

(74) *Attorney, Agent, or Firm* — Stinson Leonard Street LLP

(57) ABSTRACT

The invention concerns soluble variants of *Treponema pallidum* antigen 47 (TpN47 antigen) comprising at least domain B, or at least domains A and B, optionally domain D of the complete TpN47 protein molecule with the proviso that all antigens lack domain C (amino acid residues 224 to 351) of TpN47. The Tpn47 antigens can be fused to a chaperone. Moreover, the invention covers DNA encoding the antigens, a method of producing these antigens as well as the use of these antigens in an immunodiagnostic assay for the detection of antibodies against *Treponema pallidum* in an isolated sample.

15 Claims, 14 Drawing Sheets

Table 2

Figure 8a

| experiment | 1 | | 2 | | 3 | | 10 | |
|---|---|---|---|---|---|---|---|---|
| R1 | rec. *Ec*SlyD- | | rec. *Ec*SlyD- | | rec. *Ec*SlyD- | | rec. *Ec*SlyD- | |
| | **TpN47 (30-66)** | | **TpN47 (106-132)** | | **TpN47 (137-170)** | | **TpN47 (21-434)** | |
| label | Bi(DDS) | | Bi(DDS) | | Bi(DDS) | | Bi(DDS) | |
| concentration Bi-conjugate | 70 ng/ml | | 70 ng/ml | | 70 ng/ml | | 70 ng/ml | |
| R2 | rec. *Ec*SlyD- | | rec. *Ec*SlyD- | | rec. *Ec*SlyD- | | rec. *Ec*SlyD- | |
| | **TpN47(30-66)** | | **TpN47(106-132)** | | **TpN47(137-170)** | | **TpN47(21-434)** | |
| label | BPRu(SK(2)DSS) | | BPRu(SK(2)DSS) | | BPRu(SK(2)DSS) | | BPRu(SK(2)DSS) | |
| concentration Ru-conjugate | 70 ng/ml | | 70 ng/ml | | 70 ng/ml | | 70 ng/ml | |
| **sample** | signal | signal dynamics | signal | signal dyn. | signal | signal dyn. | signal | signal dyn. |
| average neg. sera | 491 | 1.00 | 511 | 1.00 | 501 | 1.00 | 900 | 1.00 |
| int. donor 4320 | 488 | 0.99 | 486 | 0.95 | 493 | 0.98 | 534 | 0.59 |
| int. donor 4321 | 496 | 1.01 | 523 | 1.02 | 508 | 1.01 | 524 | 0.58 |
| int. donor 4322 | 521 | 1.06 | 609 | 1.19 | 555 | 1.11 | 1,197 | 1.33 |
| int. donor 4511 | 489 | 1.00 | 507 | 0.99 | 486 | 0.97 | 521 | 0.58 |
| int. donor 4316 | 493 | 1.00 | 493 | 0.97 | 491 | 0.98 | 520 | 0.58 |
| int. donor 4345 | 496 | 1.01 | 512 | 1.00 | 514 | 1.03 | 1,321 | 1.47 |
| int. donor 4314 | 468 | 0.95 | 476 | 0.93 | 486 | 0.97 | 602 | 0.67 |
| int. donor 4474 | 473 | 0.96 | 487 | 0.95 | 485 | 0.97 | 543 | 0.60 |
| int. donor 4475 | 492 | 1.00 | 513 | 1.00 | 504 | 1.01 | 2,694 | 2.99 |
| int. donor 4476 | 492 | 1.00 | 502 | 0.98 | 489 | 0.98 | 545 | 0.61 |
| Syhilis IgG 1209A179 | 1,543 | 3.14 | 524 | 1.03 | 520 | 1.04 | 91,925 | 102.13 |
| Syhilis IgG 1209A178 | 1,220 | 2.49 | 511 | 1.00 | 524 | 1.05 | 10,326 | 11.47 |
| Syhilis IgG 1209A177 | 8,601 | 17.52 | 962 | 1.88 | 794 | 1.58 | 200.660 | 222.93 |
| Syhilis IgG 1209A176 | 678 | 1.38 | 486 | 0.95 | 513 | 1.02 | 37,500 | 41.66 |
| Syhilis IgG 1209A174 | 718 | 1.46 | 489 | 0.96 | 505 | 1.01 | 225,310 | 250.32 |
| Syhilis IgM 1209A192 | 8,201 | 16.71 | 590 | 1.16 | 1,603 | 3.20 | 171,322 | 190.34 |
| Syhilis IgM 1209A191 | 10,513 | 21.42 | 807 | 1.58 | 830 | 1.66 | 109,434 | 121.58 |
| Syhilis IgM 1209A188 | 18,647 | 37.99 | 498 | 0.97 | 496 | 0.99 | 160,090 | 177.88 |
| Syhilis IgM 1209A167 | 507 | 1.03 | 514 | 1.01 | 526 | 1.05 | 9,991 | 11.10 |
| Syhilis IgM 1209A166 | 62,458 | 127.26 | 5,760 | 11.28 | 1,700 | 3.39 | 164,024 | 182.23 |

Table 2 Figure 8b

| experiment | 4 | | 5 | | 6 | | 10 | |
|---|---|---|---|---|---|---|---|---|
| R1 | rec. *Ec*SlyD- | | rec. *Ec*SlyD- | | rec. *Ec*SlyD- | | rec. *Ec*SlyD- | |
| | **TpN47 (197-219)** | | **TpN47 (225-250)** | | **TpN47 (273-296)** | | **TpN47 (21-434)** | |
| label | Bi(DDS) | | Bi(DDS) | | Bi(DDS) | | Bi(DDS) | |
| concentration Bi-conjugate | 70 ng/ml | | 70 ng/ml | | 70 ng/ml | | 70 ng/ml | |
| R2 | rec. *Ec*SlyD- | | rec. *Ec*SlyD- | | rec. *Ec*SlyD- | | rec. *Ec*SlyD- | |
| | **TpN47(197-219)** | | **TpN47(225-250)** | | **TpN47(273-296)** | | **TpN47(21-434)** | |
| label | BPRu(SK(2)DSS) | | BPRu(SK(2)DSS) | | BPRu(SK(2)DSS) | | BPRu(SK(2)DSS) | |
| concentration Ru-conjugate | 70 ng/ml | | 70 ng/ml | | 70 ng/ml | | 70 ng/ml | |
| **sample** | signal | signal dyn. | signal | signal dyn. | signal | signal dyn. | signal | signal dyn. |
| average neg. sera | 503 | 1.00 | 497 | 1.00 | 506 | 1.00 | 900 | 1.00 |
| int. donor 4320 | 496 | 0.99 | 494 | 0.99 | 504 | 1.00 | 534 | 0.59 |
| int. donor 4321 | 507 | 1.01 | 500 | 1.01 | 524 | 1.04 | 524 | 0.58 |
| int. donor 4322 | 545 | 1.08 | 515 | 1.04 | 558 | 1.10 | 1,197 | 1.33 |
| int. donor 4511 | 497 | 0.99 | 493 | 0.99 | 512 | 1.01 | 521 | 0.58 |
| int. donor 4316 | 487 | 0.97 | 496 | 1.00 | 487 | 0.96 | 520 | 0.58 |
| int. donor 4345 | 516 | 1.03 | 511 | 1.03 | 512 | 1.01 | 1,321 | 1.47 |
| int. donor 4314 | 477 | 0.95 | 479 | 0.96 | 477 | 0.94 | 602 | 0.67 |
| int. donor 4474 | 483 | 0.96 | 498 | 1.00 | 497 | 0.98 | 543 | 0.60 |
| int. donor 4475 | 521 | 1.04 | 491 | 0.99 | 497 | 0.98 | 2,694 | 2.99 |
| int. donor 4476 | 502 | 1.00 | 492 | 0.99 | 488 | 0.97 | 545 | 0.61 |
| Syhilis IgG 1209A179 | 508 | 1.01 | 510 | 1.03 | 515 | 1.02 | 91,925 | 102.13 |
| Syhilis IgG 1209A178 | 506 | 1.01 | 488 | 0.98 | 507 | 1.00 | 10,326 | 11.47 |
| Syhilis IgG 1209A177 | 631 | 1.25 | 556 | 1.12 | 640 | 1.27 | 200,660 | 222.93 |
| Syhilis IgG 1209A176 | 503 | 1.00 | 495 | 1.00 | 508 | 1.00 | 37,500 | 41.66 |
| Syhilis IgG 1209A174 | 486 | 0.97 | 493 | 0.99 | 487 | 0.96 | 225,310 | 250.32 |
| Syhilis IgM 1209A192 | 533 | 1.06 | 505 | 1.02 | 516 | 1.02 | 171,322 | 190.34 |
| Syhilis IgM 1209A191 | 643 | 1.28 | 616 | 1.24 | 564 | 1.12 | 109,434 | 121.58 |
| Syhilis IgM 1209A188 | 495 | 0.98 | 468 | 0.94 | 492 | 0.97 | 160,090 | 177.86 |
| Syhilis IgM 1209A167 | 523 | 1.04 | 507 | 1.02 | 515 | 1.02 | 9,991 | 11.10 |
| Syhilis IgM 1209A166 | 985 | 1.96 | 769 | 1.55 | 1,133 | 2.24 | 164,024 | 182.23 |

Table 2 Figure 8c

| experiment | 7 | | 8 | | 9 | | 10 | |
|---|---|---|---|---|---|---|---|---|
| R1 | rec. *Ec*SlyD- | | rec. *Ec*SlyD- | | rec. *Ec*SlyD- | | rec. *Ec*SlyD- | |
| | **TpN47 (321-362)** | | **TpN47 (368-388)** | | **TpN47 (391-434)** | | **TpN47 (21-434)** | |
| label | Bi(DDS) | | Bi(DDS) | | Bi(DDS) | | Bi(DDS) | |
| concentration Bi-conjugate | 70 ng/ml | | 70 ng/ml | | 70 ng/ml | | 70 ng/ml | |
| R2 | rec. *Ec*SlyD- | | rec. *Ec*SlyD- | | rec. *Ec*SlyD- | | rec. *Ec*SlyD- | |
| | **TpN47(321-362)** | | **TpN47(368-388)** | | **TpN47(391-434)** | | **TpN47(21-434)** | |
| label | BPRu(SK(2)DSS) | | BPRu(SK(2)DSS) | | BPRu(SK(2)DSS) | | BPRu(SK(2)DSS) | |
| concentration Ru-conjugate | 70 ng/ml | | 70 ng/ml | | 70 ng/ml | | 70 ng/ml | |
| **sample** | signal | signal dyn. | signal | signal dyn. | signal | signal dyn. | signal | signal dyn. |
| average neg. sera | 498 | 1.00 | 489 | 1.00 | 518 | 1.00 | 900 | 1.00 |
| int. donor 4320 | 489 | 0.98 | 482 | 0.99 | 502 | 0.97 | 534 | 0.59 |
| int. donor 4321 | 503 | 1.01 | 495 | 1.01 | 521 | 1.01 | 524 | 0.58 |
| int. donor 4322 | 553 | 1.11 | 518 | 1.06 | 577 | 1.11 | 1,197 | 1.33 |
| int. donor 4511 | 488 | 0.98 | 478 | 0.98 | 531 | 1.02 | 521 | 0.58 |
| int. donor 4316 | 476 | 0.96 | 487 | 1.00 | 503 | 0.97 | 520 | 0.58 |
| int. donor 4345 | 500 | 1.01 | 496 | 1.01 | 530 | 1.02 | 1.321 | 1.47 |
| int. donor 4314 | 478 | 0.96 | 473 | 0.97 | 485 | 0.94 | 602 | 0.67 |
| int. donor 4474 | 491 | 0.99 | 490 | 1.00 | 514 | 0.99 | 543 | 0.60 |
| int. donor 4475 | 495 | 0.99 | 478 | 0.98 | 503 | 0.97 | 2,694 | 2.99 |
| int. donor 4476 | 502 | 1.01 | 492 | 1.01 | 517 | 1.00 | 545 | 0.61 |
| Syhilis IgG 1209A179 | 508 | 1.02 | 492 | 1.01 | 515 | 0.99 | 91,925 | 102.13 |
| Syhilis IgG 1209A178 | 487 | 0.98 | 494 | 1.01 | 523 | 1.01 | 10,326 | 11.47 |
| Syhilis IgG 1209A177 | 635 | 1.28 | 556 | 1.14 | 845 | 1.63 | 200,660 | 222.93 |
| Syhilis IgG 1209A176 | 507 | 1.02 | 492 | 1.01 | 528 | 1.02 | 37,500 | 41.66 |
| Syhilis IgG 1209A174 | 490 | 0.98 | 468 | 0.96 | 500 | 0.96 | 225,310 | 250.32 |
| Syhilis IgM 1209A192 | 498 | 1.00 | 485 | 0.99 | 576 | 1.11 | 171,322 | 190.34 |
| Syhilis IgM 1209A191 | 480 | 0.96 | 589 | 1.20 | 688 | 1.33 | 109,434 | 121.58 |
| Syhilis IgM 1209A188 | 482 | 0.97 | 483 | 0.99 | 509 | 0.98 | 160,090 | 177.86 |
| Syhilis IgM 1209A167 | 506 | 1.02 | 514 | 1.05 | 531 | 1.02 | 9,991 | 11.10 |
| Syhilis IgM 1209A166 | 1,282 | 2.58 | 720 | 1.47 | 1,656 | 3.20 | 164,024 | 182.23 |

Table 3

Figure 9

| R1: *Ec*SlyD-*Ec*SlyD-[TpN47 domain]-Biotin | **AB (26-223)** | | **B (63-174)** | | **C (224-351)** | | **D (352-434)** | | **CD (224-434)** | | **ABCD (21-434)** | |
|---|---|---|---|---|---|---|---|---|---|---|---|---|
| R2: *Ec*SlyD-*Ec*SlyD-[TpN47 domain]-Ru | **AB (26-223)** | | **B (63-174)** | | **C (224-351)** | | **D (352-434)** | | **CD (224-434)** | | **ABCD (21-434)** | |
| conc. Bi/Ru conjugate | 70 ng/ml | | 70 ng/ml | | 70 ng/ml | | 70 ng/ml | | 70 ng/ml | | 70 ng/ml | |
| **sample** | sig [cts] | signal dyn. | sig [cts] | signal dyn | sig [cts] | signal dyn | sig [cts] | signal dyn | sig [cts] | signal dyn | sig [cts] | signal dyn |
| average neg. sera | 454 | | 467 | | 594 | | 472 | | 541 | | 515 | |
| int. donor 4320 | 453 | 1.00 | 476 | 1.02 | 580 | 0.98 | 477 | 1.01 | 529 | 0.98 | 518 | 1.01 |
| int. donor 4321 | 463 | 1.02 | 476 | 1.02 | 608 | 1.02 | 482 | 1.02 | 551 | 1.02 | 528 | 1.02 |
| int. donor 4322 | 468 | 1.03 | 476 | 1.02 | 623 | 1.05 | 481 | 1.02 | 557 | 1.03 | 525 | 1.02 |
| int. donor 4475 | 449 | 0.99 | 467 | 1.00 | 588 | 0.99 | 471 | 1.00 | 542 | 1.00 | 519 | 1.01 |
| int. donor 4474 | 444 | 0.98 | 465 | 1.00 | 591 | 1.00 | 459 | 0.97 | 551 | 1.02 | 519 | 1.01 |
| int. donor 4345 | 465 | 1.02 | 455 | 0.97 | 574 | 0.97 | 509 | 1.08 | 538 | 0.99 | 508 | 0.99 |
| int. donor 4314 | 449 | 0.99 | 455 | 0.97 | 596 | 1.00 | 448 | 0.95 | 527 | 0.98 | 494 | 0.96 |
| int. donor 4511 | 452 | 1.00 | 466 | 1.00 | 594 | 1.00 | 470 | 1.00 | 537 | 0.99 | 507 | 0.99 |
| int. donor 4316 | 447 | 0.98 | 460 | 0.98 | 588 | 0.99 | 456 | 0.97 | 534 | 0.99 | 503 | 0.98 |
| int. donor 4476 | 453 | 1.00 | 478 | 1.02 | 596 | 1.00 | 462 | 0.98 | 540 | 1.00 | 527 | 1.02 |
| Syphilis IgG 1209A179 | 12,359 | 27.21 | 7,615 | 16.30 | 596 | 1.00 | 11,616 | 24.63 | 15,227 | 28.17 | 29,592 | 57.49 |
| Syphilis IgG 1209A178 | 2,356 | 5.19 | 1,393 | 2.98 | 596 | 1.00 | 850 | 1.80 | 1,087 | 2.01 | 3,260 | 6.33 |
| Syphilis IgG 1209A177 | 60,282 | 132.72 | 41,889 | 89.63 | 563 | 0.95 | 13,094 | 27.77 | 17,530 | 32.43 | 94,880 | 184.32 |
| Syphilis IgG 1209A176 | 8,447 | 18.60 | 6,204 | 13.27 | 607 | 1.02 | 1,773 | 3.76 | 2,014 | 3.73 | 11,894 | 23.11 |
| Syphilis IgG 1209A174 | 44,791 | 98.61 | 35,280 | 75.49 | 595 | 1.00 | 37,192 | 78.87 | 48,197 | 89.15 | 104,758 | 203.51 |
| Syphilis IgM 1209A192 | 75,638 | 166.53 | 31,696 | 67.82 | 881 | 1.48 | 13,250 | 28.10 | 26,668 | 49.33 | 124,027 | 240.94 |
| Syphilis IgM 1209A191 | 121,724 | 267.99 | 77,708 | 166.28 | 608 | 1.02 | 38,260 | 81.13 | 58,394 | 108.01 | 150,789 | 292.93 |
| Syphilis IgM 1209A188 | 45,905 | 101.07 | 23,721 | 50.76 | 582 | 0.98 | 1,569 | 3.33 | 2,895 | 5.36 | 62,311 | 121.05 |
| Syphilis IgM 1209A167 | 1,216 | 2.68 | 829 | 1.77 | 613 | 1.03 | 507 | 1.08 | 674 | 1.25 | 1,887 | 3.67 |
| Syphilis IgM 1209A166 | 162,863 | 358.57 | 81,235 | 173.82 | 644 | 1.08 | 38,163 | 80.93 | 58,444 | 108.11 | 178,318 | 346.41 |

Table 4

Figure 10

| R1 | *Ec*SlyD-*Ec*SlyD-TpN47[AB] -Bi | | | | | *Ec*SlyD-*Ec*SlyD-TpN47 [B] -Bi | | | | |
|---|---|---|---|---|---|---|---|---|---|---|
| | TpN47 (26-223) | | | | | TpN47 (63-174) | | | | |
| | 70ng/ml | | | | | 70ng/ml | | | | |
| Thermal stress | 72h 4°C | | 72h 42°C | | signal recovery | 72h 4°C | | 72h 42°C | | signal recovery |
| R2 | *Ec*SlyD-*Ec*SlyD-TpN47 [AB] -Ru | | | | | *Ec*SlyD-*Ec*SlyD-TpN47 [B] -Ru | | | | |
| | TpN47 (26-223) | | | | | TpN47 (63-174) | | | | |
| | 70ng/ml | | | | | 70ng/ml | | | | |
| Thermal stress | 72h 4°C | | 72h 42°C | | signal recovery | 72h 4°C | | 72h 42°C | | signal recovery |
| | cts | SD | cts | SD | | cts | SD | cts | SD | |
| BM 200830 | 2,859 | 6.37 | 2,114 | 4.67 | 73.9% | 1,571 | 3.33 | 1,475 | 3.15 | 93.9% |
| BM 200831 | 2,892 | 6.44 | 2,661 | 5.88 | 92.0% | 1,862 | 3.94 | 1,768 | 3.78 | 94.9% |
| BM 202017 | 47,659 | 106 | 42,159 | 93.1 | 88.5% | 45,895 | 97.2 | 42,945 | 91.8 | 93.6% |
| BM 202018 | 37,619 | 83.8 | 33,297 | 73.5 | 88.5% | 36,750 | 77.8 | 33,793 | 72.2 | 92.0% |
| BM 206252 | 17,346 | 38.7 | 15,372 | 33.9 | 88.6% | 10,361 | 21.9 | 9,617 | 20.5 | 92.8% |
| BM 206253 | 18,178 | 40.5 | 15,656 | 34.6 | 86.1% | 10,606 | 22.5 | 9,763 | 20.9 | 92.1% |
| BM 206254 | 23,179 | 51.6 | 20,424 | 45.1 | 88.1% | 13,492 | 28.6 | 12,700 | 27.1 | 94.1% |
| Trina #097 | 447 | 1.00 | 447 | 0.987 | 100% | 478 | 1.01 | 468 | 0.999 | 97.8% |
| Trina #098 | 450 | 1.00 | 467 | 1.03 | 104% | 462 | 0.979 | 463 | 0.990 | 100% |
| Trina #099 | 449 | 1.00 | 460 | 1.02 | 102% | 482 | 1.02 | 471 | 1.01 | 97.6% |
| Trina #100 | 450 | 1.00 | 437 | 0.966 | 97.3% | 466 | 0.987 | 470 | 1.01 | 101% |
| average negative | 449 | | 453 | | | 472 | | 468 | | |

Table 5

Figure 11

| R1 | *Ec*SlyD-*Ec*SlyD-TpN47[C] -Bi | | | | | *Ec*SlyD-*Ec*SlyD-TpN47[D] -Bi | | | | |
|---|---|---|---|---|---|---|---|---|---|---|
| | TpN47 (224-351) | | | | | TpN47 (352-434) | | | | |
| | 70ng/ml | | | | | 70ng/ml | | | | |
| Thermal stress | 72h 4°C | | 72h 42°C | | signal recovery | 72h 4°C | | 72h 42°C | | signal recovery |
| R2 | *Ec*SlyD-*Ec*SlyD-TpN47 [C] -Ru | | | | | *Ec*SlyD-*Ec*SlyD-TpN47 [D] -Ru | | | | |
| | TpN47 (224-351) | | | | | TpN47 (352-434) | | | | |
| | 70ng/ml | | | | | 70ng/ml | | | | |
| Thermal stress | 72h 4°C | | 72h 42°C | | signal recovery | 72h 4°C | | 72h 42°C | | signal recovery |
| | cts | SD | cts | SD | | cts | SD | cts | SD | |
| BM 200830 | 619 | 1.01 | 658 | 1.03 | 106% | 1,417 | 3.02 | 1,424 | 3.03 | 100% |
| BM 200831 | 618 | 1.01 | 665 | 1.04 | 108% | 1,684 | 3.59 | 1,673 | 3.56 | 99.3%. |
| BM 202017 | 643 | 1.06 | 660 | 1.03 | 103%. | 5,031 | 10.7 | 5,133 | 10.9 | 102%. |
| BM 202018 | 612 | 1.00 | 670 | 1.05 | 109%. | 4,009 | 8.54 | 4,180 | 8.91 | 104%. |
| BM 206252 | 655 | 1.07 | 669 | 1.05 | 102%. | 2,264 | 4.82 | 2,370 | 5.05 | 105%. |
| BM 206253 | 624 | 1.02 | 659 | 1.03 | 106%. | 2,301 | 4.90 | 2,366 | 5.04 | 103%. |
| BM 206254 | 623 | 1.02 | 655 | 1.03 | 105%. | 2,733 | 5.82 | 2,844 | 6.06 | 104%. |
| Trina #097 | 607 | 1.00 | 648 | 1.01 | 107%. | 460 | 0.98 | 459 | 0.98 | 99.6%. |
| Trina #098 | 614 | 1.01 | 626 | 0.981 | 102%. | 475 | 1.01 | 480 | 1.02 | 101%. |
| Trina #099 | 610 | 1.00 | 645 | 1.01 | 106%. | 469 | 1.00 | 468 | 1.00 | 99.7%. |
| Trina #100 | 608 | 1.00 | 635 | 0.995 | 104%. | 472 | 1.01 | 471 | 1.00 | 99.7%. |
| average negative | 610 | | 638 | | | 469 | | 469 | | |

Figure 12

Table 6

| R1 | ***Ec*SlyD-*Ec*SlyD-TpN47[CD] -Bi** | | | | | ***Ec*SlyD-*Ec*SlyD-TpN47[ABCD] -Bi** | | | | |
|---|---|---|---|---|---|---|---|---|---|---|
| | **TpN47 (224-434)** | | | | | **full-length TpN47 (21-434)** | | | | |
| | 70ng/ml | | | | | 70ng/ml | | | | |
| thermal stress | 72h 4°C | | 72h 42°C | | signal recovery | 72h 4°C | | 72h 42°C | | signal recovery |
| R2 | ***Ec*SlyD-*Ec*SlyD-TpN47[CD] -Ru** | | | | | ***Ec*SlyD-*Ec*SlyD-TpN47[ABCD] -Ru** | | | | |
| | **TpN47 (224-434)** | | | | | **full-length TpN47 (21-434)** | | | | |
| | 70ng/ml | | | | | 70ng/ml | | | | |
| thermal stress | 72h 4°C | | 72h 42°C | | signal recovery | 72h 4°C | | 72h 42°C | | signal recovery |
| | cts | SD | cts | SD | | cts | SD | cts | SD | |
| BM 200830 | 1,803 | 3.41 | 1,442 | 2.67 | 80.0% | 4,250 | 8.50 | 2,217 | 4.08 | 52.2% |
| BM 200831 | 2,272 | 4.30 | 1,775 | 3.29 | 78.1%. | 5,383 | 10.8 | 2,609 | 4.80 | 48.5%. |
| BM 202017 | 7,532 | 14.3 | 5,116 | 9.48 | 67.9%. | 77,703 | 155 | 44,871 | 82.5 | 57.7%. |
| BM 202018 | 5,967 | 11.3 | 4,044 | 7.49 | 67.8%. | 62,711 | 125 | 36,044 | 66.3 | 57.5%. |
| BM 206252 | 3,531 | 6.68 | 2,550 | 4.72 | 72.2%. | 22,806 | 45.6 | 10,179 | 18.7 | 44.6%. |
| BM 206253 | 3,465 | 6.56 | 2,565 | 4.75 | 74.0%. | 23,101 | 46.2 | 10,556 | 19.4 | 45.7%. |
| BM 206254 | 4,231 | 8.01 | 2,958 | 5.48 | 69.9%. | 29,093 | 58.2 | 13,151 | 24.2 | 45.2%. |
| Trina #097 | 531 | 1.006 | 536 | 0.993 | 101%. | 492 | 0.984 | 540 | 0.992 | 110%. |
| Trina #098 | 531 | 1.005 | 539 | 0.998 | 101%. | 499 | 0.998 | 546 | 1.00 | 109%. |
| Trina #099 | 526 | 0.995 | 548 | 1.014 | 104%. | 505 | 1.011 | 547 | 1.01 | 108%. |
| Trina #100 | 525 | 0.994 | 537 | 0.995 | 102%. | 503 | 1.006 | 542 | 0.997 | 108%. |
| average negative | 528 | | 540 | | | 500 | | 544 | | |

SOLUBLE IMMUNOREACTIVE TREPONEMA PALLIDUM TPN47 ANTIGENS

RELATED APPLICATIONS

This application is a continuation of International Patent Application No. PCT/EP2013/000108 filed Jan. 16, 2013, which claims the benefit of European Patent Application No. 12000310.8; filed Jan. 19, 2012, the disclosures of which are hereby incorporated by reference in their entirety.

FIELD OF THE INVENTION

The invention concerns soluble, stable and immunoreactive variants of *Treponema pallidum* antigen 47 (TpN47) comprising at least amino acid residues 63 to 174 (i.e. domain B) of the TpN47 protein molecule with the proviso that the antigens lack amino acids 224 to 351 (i.e. domain C) of TpN47, wherein the TpN47 antigen is fused with a chaperone. The invention further concerns a soluble *Treponema pallidum* antigen 47 (TpN47 antigen) comprising domains B and D or domains A+B and D, also with the proviso that these antigens lack domain C. Moreover, the invention concerns a method of producing these soluble, stable and immune-reactive TpN47 variants as well as the use of these antigens in an immunodiagnostic assay aiming at the detection of antibodies against *Treponema pallidum* in an isolated sample.

BACKGROUND OF THE INVENTION

*Treponema pallidum* belongs to the bacterial family of spirochetes and is the causative agent of syphilis. Syphilis, also called Lues, is mainly transmitted by sexual contact. *Treponema pallidum* can also pass from mother to baby during pregnancy. The disease is characterized by distinct clinical stages and long periods of latent, asymptomatic infection. Many people do not notice symptoms and thus are unaware of their syphilis infection for years. The primary infection is confined and usually causes a small painless ulcer (primary stage, "Lues I"). If left untreated by penicillin, the disease proceeds to the secondary stage Lues II (about eight weeks after infection), which entails flu-like symptoms, non-itchy skin rash and swollen lymph nodes. After some years, at stage Lues III, syphilitic nodes appear throughout the body. The final stage (Lues IV) is characterized by destruction of the central nervous system eventually leading to neurological and cardiological disorders, general paralysis, ataxia, dementia and blindness.

Although effective therapies have been available since the introduction of penicillin in the mid-20th century, syphilis still remains an important global health problem. It is mandatory to identify patients with *Treponema* infection, to support antibiotic therapy and thus to prevent spread of syphilis. As a consequence, it is necessary to provide reliable diagnostic tools such as immunoassays for the detection of antibodies against *Treponema pallidum*. Yet, in order to be used as specific compounds in serological applications, recombinant proteins have to meet several requirements such as solubility, stability and antigenicity.

One of the membrane-associated polypeptides of *Treponema pallidum* (the causative agent of Syphilis infections) is TpN47, a large protein that consists of 434 amino acid residues. TpN47 has been ascribed immunodominance in the humoral immune response against *Treponema* (N Rostopira et al., Folia Microbiol. (2003) 48 (4), 549-553), and antibodies towards TpN47 are frequently found in human sera from *Treponema*-infected individuals. Thus, a soluble and antigenic variant of recombinant TpN47 would be an invaluable ingredient to establish an immunoassay for detection of *Treponema* antibodies that combines high sensitivity and specificity. In the best case, such an antigen should enable the detection of both IgG and IgM molecules.

Recombinant variants of TpN47 have been described in literature. In the Journal of Immunology (1996) July 15; 157(2):720-31, Baughn et al. report on an epitope scan of 12-mer peptides (overlap 8 amino acid residues, offset 4 amino acid residues) encompassing the entire sequence of TpN47. Based on this scan, the authors describe as many as ten immunodominant TpN47 fragments, ranging from 9 to 29 amino acid residues in length. The crystal structure and the domain topology of TpN47 has also been described (Journal of Biological Chemistry (2002), 277 (4), 41857-41864, Deka et al.). Immunoassays for detecting *Treponema* antibodies are known in the art. For example, Rostopira et al. (Folia Microbiol. 48(4), 549-553, 2003) describe an immunoassay for diagnosing syphilis using a combination of TpN17 and TpN47 antigens, identifying TpN47 as one of the immunodominant antigens. In this publication full-length TpN47 was used as an antigen.

We overproduced a full-length variant of TpN47 in an *E. coli* host (BL21/DE3) and succeeded in preparing the TpN47 antigen to homogeneity. Yet, our initial experiments with the full-length version of TpN47 unambiguously revealed that this protein tends to aggregate at temperatures above 35° C. Despite the fusion of tandem chaperone fusions such as EcSlyD-EcSlyD or even (the more thermostable) EcSlpA-EcSlpA, full-length TpN47 inevitably aggregated into a high-molecular-weight associate at temperatures above 35° C. Since *Treponema pallidum* is known as a rather temperature-sensitive pathogen, the finding that one of its major membrane proteins shares temperature sensitivity may not seem too surprising. Anyway, thermally induced aggregation processes of proteinaceous ingredients in immunoassays usually result either in a loss of signal or in a loss of specificity. Thus, the fact that full-length TpN47 (even in fusion with solubility-enhancing chaperones such as SlyD or SlpA) tends to aggregate even at moderately elevated temperatures (>35° C.), clearly precludes this molecule from simple and straightforward applications in a sensitive immunoassay of the DAGS format.

Despite the detailed structural knowledge on TpN47 (Deka et al. Journal of Biological Chemistry (2002), 277 (4), 41857-41864), the prior art does neither disclose the pronounced thermolability of TpN47 nor does it disclose TpN47 antigen variants that overcome the problem of thermally induced aggregation and the concomitant loss of sensitivity in immunoassays aiming at the detection of antibodies against *Treponema pallidum* in a sample.

Guo et al. (Xiamen Daxue Xuebao-Ziran Kexue Ban (2008), 47(6), 874-878) describe specific soluble TpN47 N- or C-terminal truncated mutants that are recombinantly expressed in *E. coli*. However, the problem of thermal instability and tendency to aggregation of full-length TpN47 protein is not addressed. In addition, the data of Guo et al. suggest that a combination of the domains C and D (C190) of TpN47 almost equals the antigenicity of the full-length TpN47 protein.

The stability problem has been solved in the current invention by generating soluble, stable and immunoreactive variants of *Treponema pallidum* antigen 47 (TpN47 antigen) comprising at least domain B (aa 63-174) of the TpN47 protein molecule with the proviso that the antigens lack domain C (aa 224-351) of TpN47, wherein the TpN47 antigen is fused with a chaperone.

A further solution of this problem is a soluble TpN47 antigen comprising domains B and D (aa 418 to 529 and 707 to 789 of SEQ ID NO. 1) or a TpN47 antigen comprising domains A+B and D (aa 381 to 578 and 707 to 789 of SEQ ID NO. 1). Both variants lack domain C of TpN47.

SUMMARY OF THE INVENTION

The invention relates to soluble *Treponema pallidum* antigens, i.e. to TpN47 antigen that comprises at least domain B (amino acid residues 418 to 529 of SEQ ID NO. 1) or at least domains A+B (amino acid residues 381 to 578 of SEQ ID NO. 1) with the proviso that the TpN47 antigen lacks domain C (amino acid residues 579 to 706 of SEQ ID NO. 1), wherein the TpN47 antigen is fused with a chaperone. The invention also relates to soluble TpN47 antigens that comprise at least domain B (amino acid residues 418 to 529 of SEQ ID NO. 1) and domain D (amino acid residues 707 to 789 of SEQ ID NO. 1), or domains A+B (amino acid residues 381 to 578 of SEQ ID NO. 1) and domain D (amino acid residues of SEQ ID NO. 1) with the proviso that these antigens also lack domain C (amino acid residues 579 to 706 of SEQ ID NO. 1). These antigens may be fused to a chaperone or to another fusion partner in order to further increase its solubility.

The invention further concerns recombinant DNA molecules encoding said TpN47 antigen and it also concerns an expression vector containing operably linked or integrated the above-described DNA encoding a TpN47 antigen. The invention also concerns a host cell transformed with said expression vector and also a method of producing said TpN47 antigen.

Moreover, the invention relates to in vitro diagnostic methods for the detection of Syphilis, i.e. to a method of detecting antibodies against TpN47 using said TpN47 antigen variants and it also relates to a reagent test kit comprising a TpN47 antigen according to the invention. The invention also relates to a composition of at least two *Treponema pallidum* antigens comprising, e.g. a TpN47 antigen and a TpN17 or a TpN15 antigen. In another embodiment said composition comprises a TpN47 antigen and both TpN17 and TpN15 antigens. Additionally, the invention concerns a method of producing these antigens as well as the use of these antigens in an immunodiagnostic assay for the detection of antibodies against *Treponema pallidum* in an isolated sample.

All of the protein constructs were subjected to elevated temperatures (35° C., 40° C.) in an overnight incubation (18 h) under identical buffer concentrations (150 mM potassium phosphate pH 8.0, 100 mM KCl, 0.5 mM EDTA) at a concentration of 1.3 mg/ml, equivalent to a molar concentration of 15.2 μM-26.5 μM. Following thermal stress, the protein samples were subjected to centrifugation and then were assessed for their tendency to aggregate by means of FPLC analysis as described above.

Figure 1:
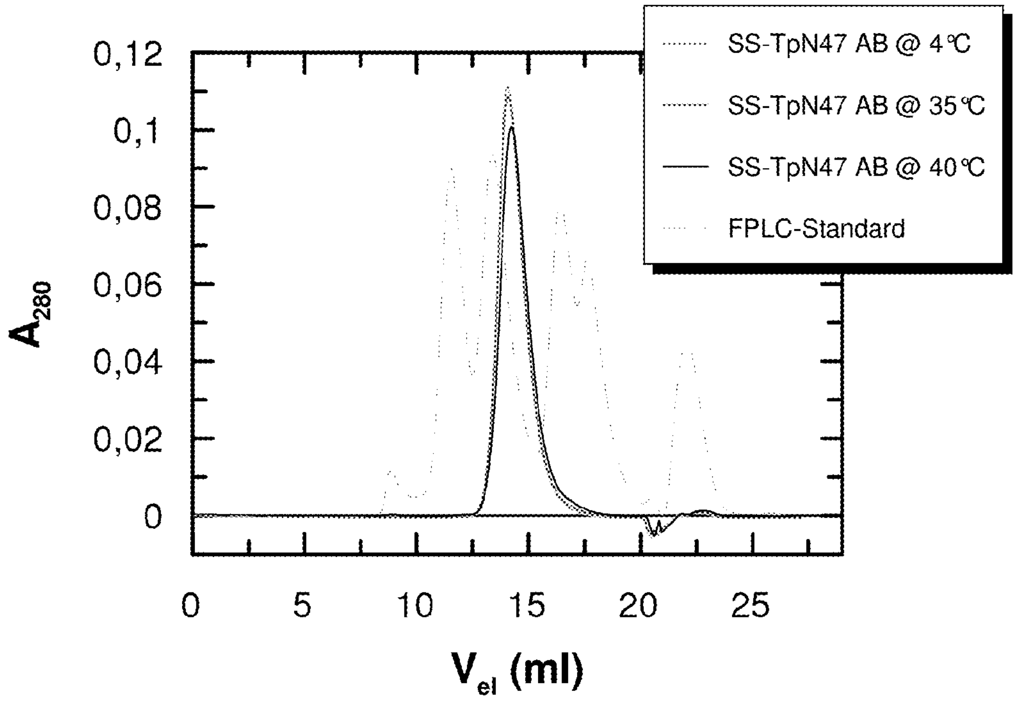
FIGS. 1-6 show analytical gel filtration profiles of distinct EcSlyD-EcSlyD-TpN47 domain constructs on a Superdex 200 HR 10/30 column, see also example 5. Ca. 200 μl of a 1.3 mg/ml protein solution (fusion protein dissolved in 150 mM potassium phosphate pH 8.0, 100 mM KCl, 0.5 mM EDTA) was applied on the SEC column, and elution was monitored at 280 nm at a flow rate of 0.8 ml/min. The FPLC standard (light gray dotted line) contains β-galactosidase (465 000 Da), sheep IgG (150 000 Da), sheep IgG Fab fragment (50 000 Da), horse myoglobin (17 000 Da), and the dipeptide glycine-tyrosine (238 Da).

FIG. 1 exhibits the thermostability of EcSlyD-EcSlyD-TpN47/AB (26-223) as assessed by analytical gel filtration on a Superdex 200 column. 230 μl were applied to the column, corresponding to 300 μg protein. Elution profiles of TpN47/AB after incubation at 4° C., 35° C. and 40° C. coincide very nicely. There is no hint to aggregation or association processes. The elution profiles as monitored by absorption at 280 nm point to a soluble protein fragment TpN47/AB even at elevated temperatures such as 40° C.

Figure 2:
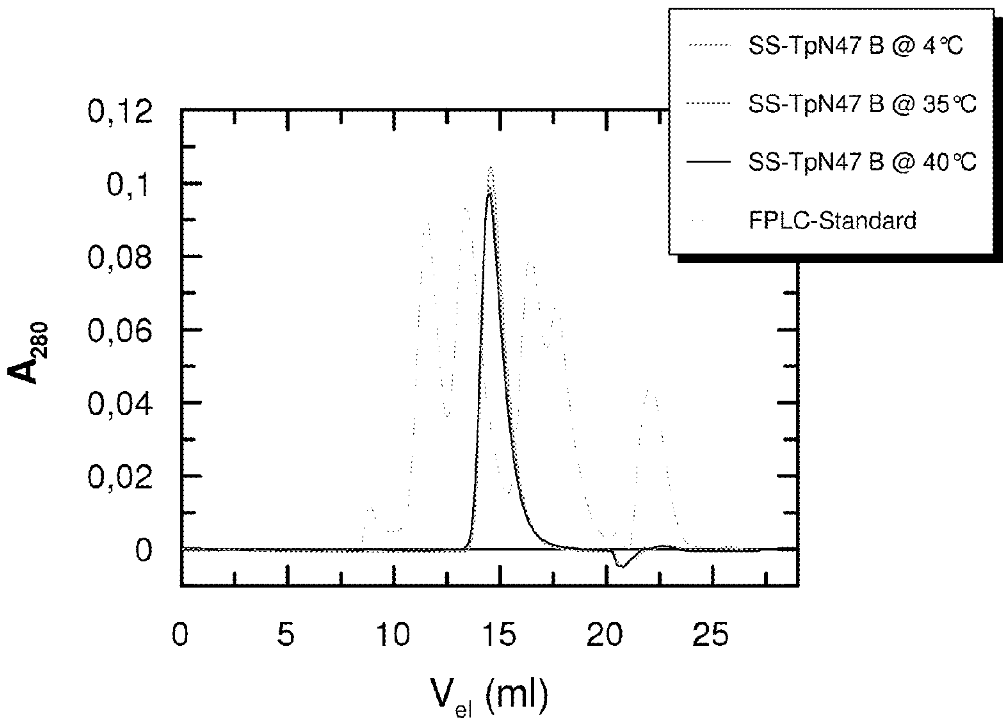

FIG. 2 shows the thermostability of EcSlyD-EcSlyD-TpN47/B (63-174) as assessed by analytical gel filtration on a Superdex 200 column. 270 μl were applied to the column, corresponding to 350 μg protein. Elution profiles of TpN47/B after incubation at 4° C., 35° C. and 40° C. coincide almost perfectly. There is no hint to aggregation or association processes. The elution profiles as monitored by absorption at 280 nm deliver compelling evidence that protein fragment TpN47/B is soluble and stable even at elevated temperatures such as 40° C.

Figure 3:
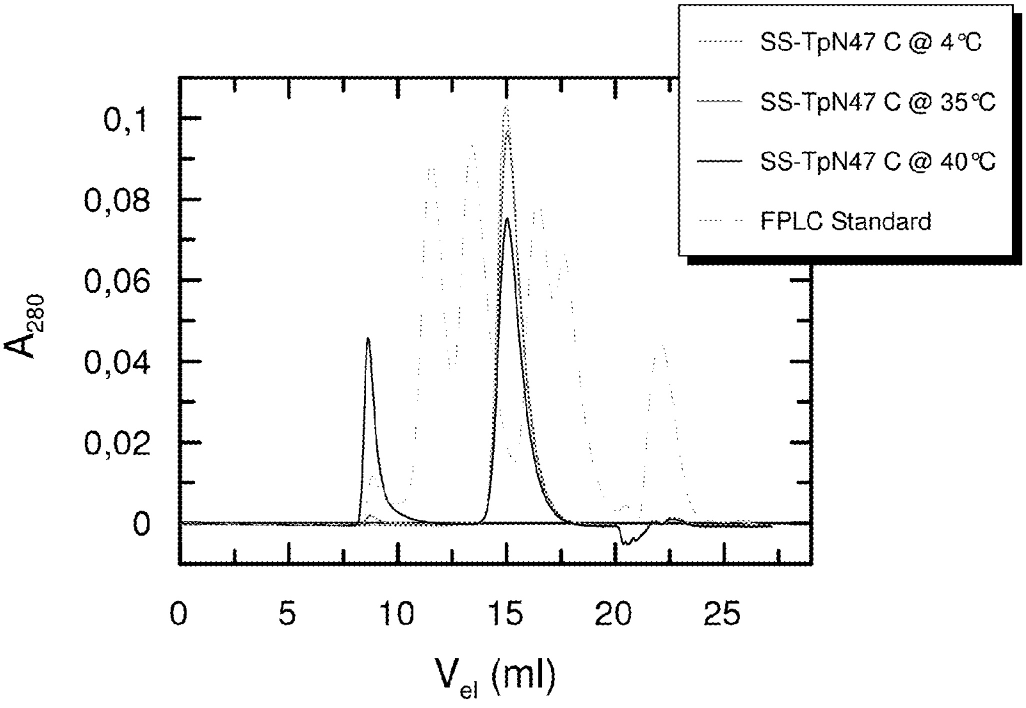

FIG. 3 illustrates the thermostability of EcSlyD-EcSlyD-TpN47/C (224-351) as assessed by analytical gel filtration on a Superdex 200 column. 154 μl were applied to the column, corresponding to 200 μg protein. Elution profiles of TpN47/C after incubation at 4° C. and 35° C. coincide almost perfectly. However, even at 35° C., a very small portion of TpN47 C elutes in the void volume of the gel filtration column (continuous dark gray line), pointing to the onset of aggregation processes. After incubation at 40° C., almost one third of the fusion protein elutes in the void volume of the SEC column, indicative of the formation of large aggregated protein particles. It becomes evident from FIG. 3 that TpN47 domain C possesses a substantial tendency to aggregate at temperatures above 35° C.

Figure 4:
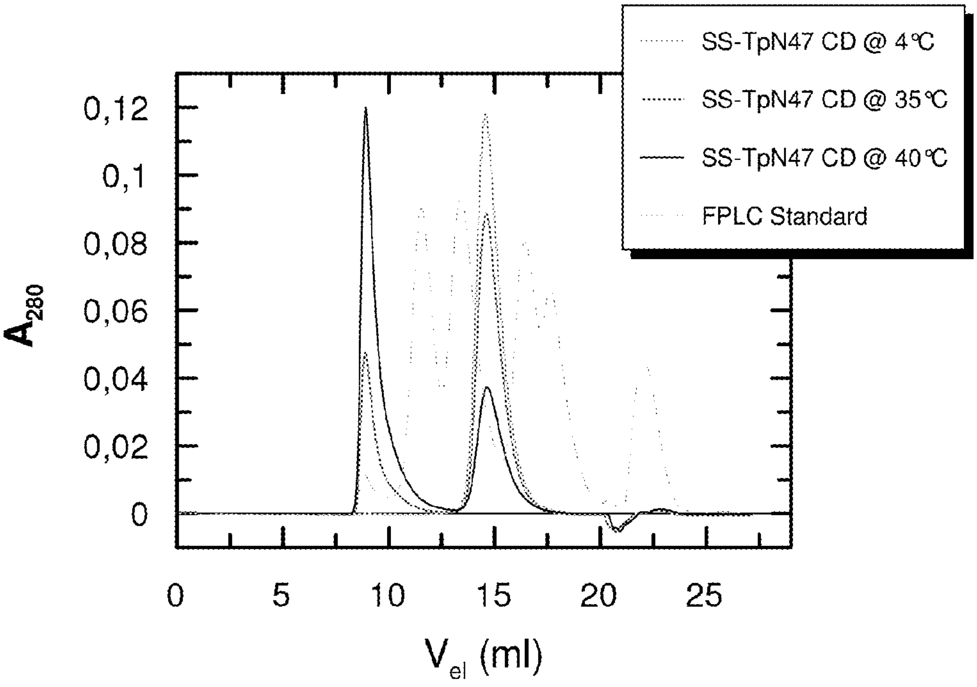

FIG. 4 shows the thermostability of EcSlyD-EcSlyD-TpN47/CD (224-434) as assessed by analytical gel filtration on a Superdex 200 column. 195 μl were applied to the column, corresponding to 250 μg protein. The elution profile of TpN47/CD after incubation at 4° C. exhibits a nice symmetrical peak, indicative of a soluble and homogeneous protein. When incubated at 35° C., EcSlyD-EcSlyD-TpN47/CD is forming large aggregated protein particles, as judged by the corresponding profile, which shows a large portion of the protein eluting in the void volume of the SEC column (continuous dark gray line). After incubation at 40° C., the lion's share of the CD fusion protein elutes in the void volume of the gel filtration column (continuous black line). It is obvious from FIG. 4 that the C-terminal part of TpN47, namely the fusion protein CD, possesses a high intrinsic tendency to aggregate even at a moderately elevated temperature such as 35° C.

Figure 5:
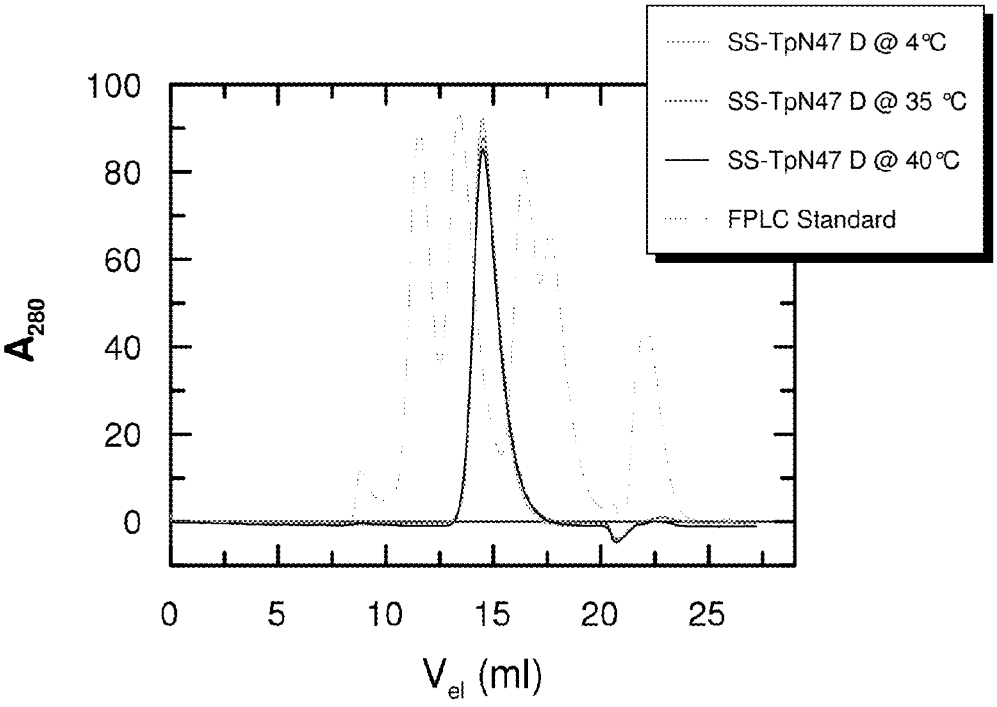

FIG. 5 illustrates the thermostability of EcSlyD-EcSlyD-TpN47/D (352-434) as assessed by analytical gel filtration on a Superdex 200 column. 331 μl were applied to the column, corresponding to 430 μg protein. Elution profiles of TpN47/D after incubation at 4° C., 35° C. and 40° C. are almost indistinguishable and coincide perfectly. There is no hint whatsoever to aggregation or association processes. The elution profiles as monitored by absorption at 280 nm deliver compelling evidence that protein fragment TpN47/D is perfectly soluble and stable even at elevated temperatures such as 40° C.

Figure 6:
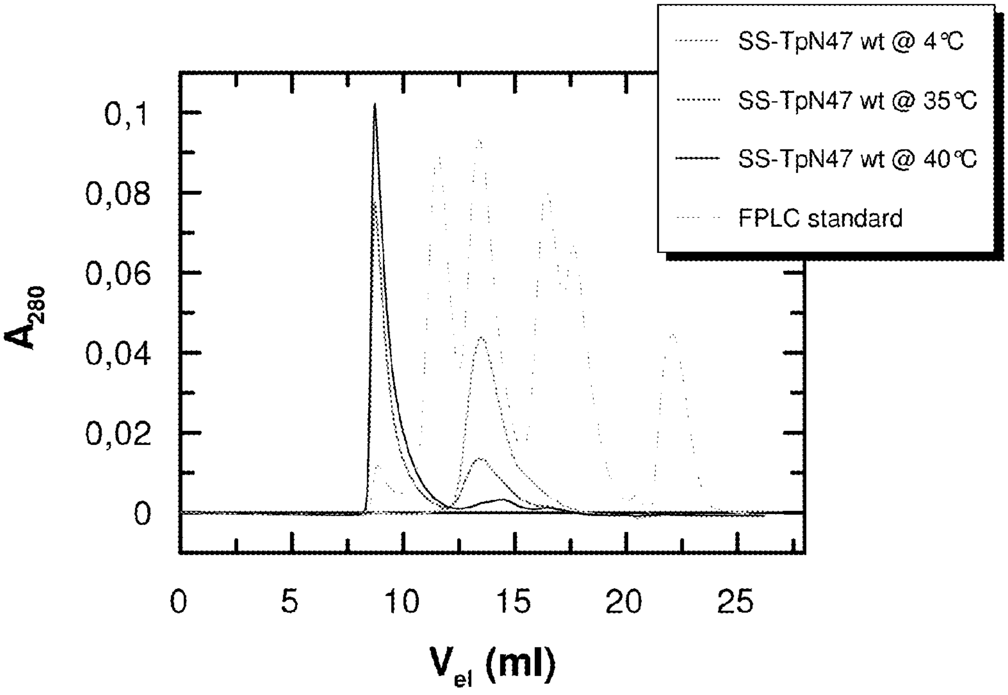

FIG. 6 shows the thermostability of the full-length TpN47 variant EcSlyD-EcSlyD-TpN47/ABCD (21-434) as assessed by analytical gel filtration on a Superdex 200 column. 90 μl were applied to the column, corresponding to 117 μg protein. The elution profile of TpN47/ABCD after incubation at 4° C. exhibits a nice peak at an elution volume of 13.5 ml, indicative of a soluble and homogeneous protein. When incubated at 35° C., EcSlyD-EcSlyD-TpN47/ABCD is forming large aggregated protein particles, as judged by the corresponding profile, which shows more than 66% of the protein eluting in the void volume of the SEC column (continuous dark gray line). After incubation at 40° C., almost 96% of full-length TpN47 elute in the void volume of the gel filtration column (continuous black line). It is obvious from FIG. 6 that full-length TpN47 possesses a tremendous intrinsic tendency to aggregate even at a moderately elevated temperature such as 35° C.

Due to a scarcity of full-length protein, only 117 μg EcSlyD-EcSlyD were applied on the Superdex column (leading to a lower absorption signal), which is only a fractional amount when compared with the other TpN47 variants. The thermal stress assessment has, however, been conducted under identical conditions for each TpN47 variant.

Figure 7:
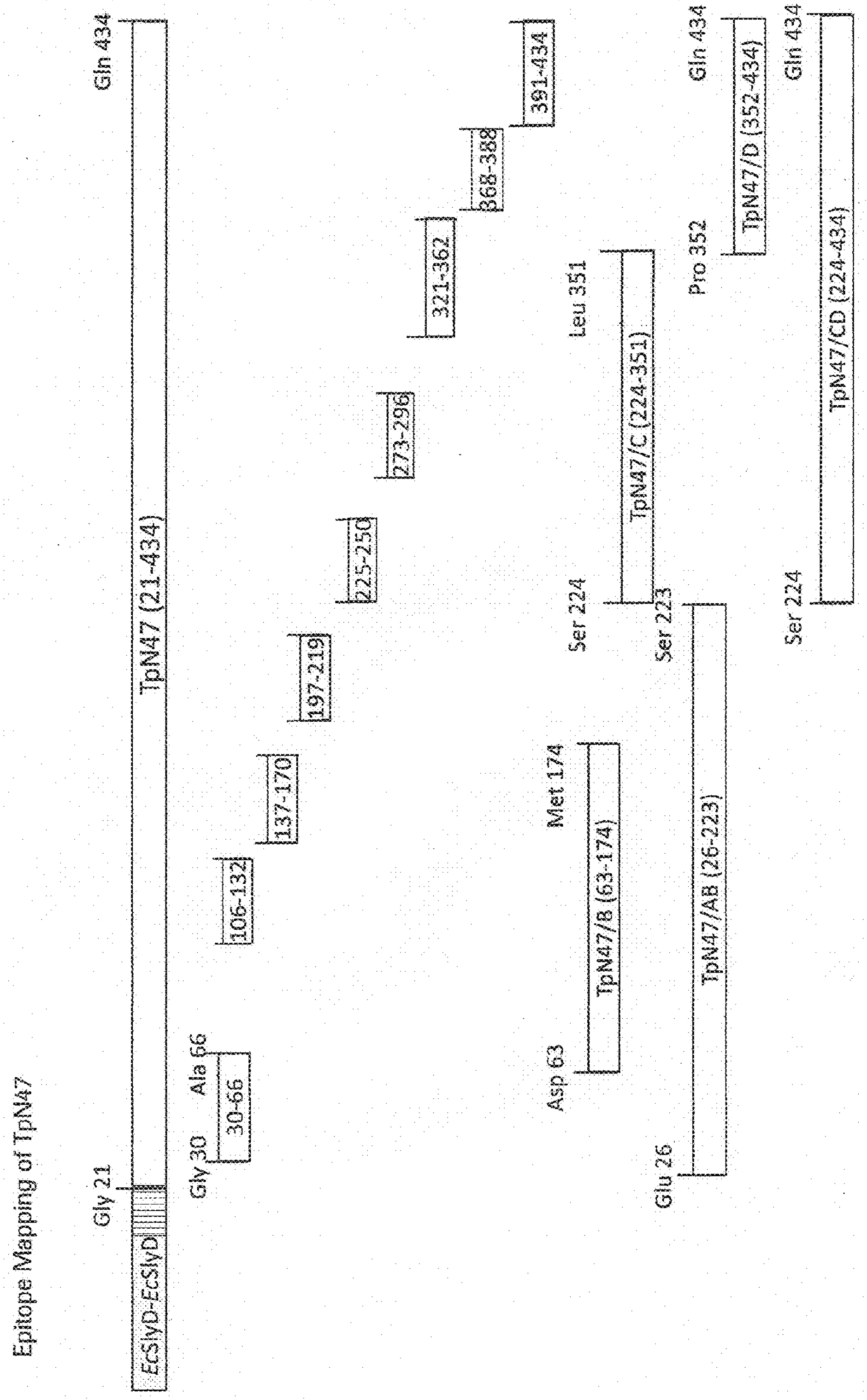

FIG. 7 shows our strategy of B-cell epitope mapping in the search for immunodominant TpN47 antigen variants. At the top: full length TpN47 (21-434, comprising domains ABCD) with EcSlyD-EcSlyD fused to the TpN47 N-terminus. Middle section: individual TpN47 polypeptide fragments (fusion to EcSlyD not shown), in ladder-like order: TpN47 polypeptide fragments 30-66, 106-132, 137-170, 197-219, 225-250, 273-296, 321-362, 368-388, 391-434 according to SEQ ID NOs. 8-16; experimental results for immunoreactivity of these peptides according to example 4 are shown in Table 2 (FIGS. 8*a-c*). Bottom: location of TpN47 domains B, AB, C, D and CD (fusion to EcSlyD-EcSlyD not shown) relative to the full length TpN47; experimental results for immunoreactivity (i.e. antigenicity) of these TpN47 fusion variants according to example 4 are shown in Table 3 (FIG. 9).

FIGS. 8*a-c* shows Table 2, containing the results obtained in example 4: Immunological reactivity of short (linear) unstructured TpN47 fragments fused to EcSlyD chaperone. The immunoassays were performed by using an Elecsys® 2010 analyzer. The signal dynamics are normalized relative to the average value obtained for the *Treponema*-negative samples. The *Treponema* positive sera were purchased from Boca Biolistics (Coconut Creek, Fla., USA), the *Treponema*-negative controls were internal blood donors. Please note that the right column (experiment 10, full length TpN47) is identical in each of FIGS. 8*a, b* and *c*, respectively.

FIG. 9 shows Table 3, containing the results obtained in example 4: Immunological reactivity (i.e. antigenicity) of large TpN47 fragments (domains) fused to EcSlyD-EcSlyD tandem chaperone. The immunoassays were performed by using an Elecsys® 2010 analyzer. The signal dynamics (SD) are normalized relative to the average value obtained for the *Treponema*-negative samples. The *Treponema*-positive sera were purchased from Boca Biolistics (Coconut Creek, Fla., USA), the negative controls were internal blood donors.

FIG. 10 shows Table 4: Residual antigenicity of TpN47 domains AB (26-223) & B (63-174) subsequent to thermal stress (72 h at 42° C.). Both domains AB and domain B were fused to the 30 solubility-enhancing tandem chaperone module EcSlyD-EcSlyD as described. The immunoassays were performed by using an Elecsys® 2010 analyzer. The signal dynamics (SD) are normalized relative to the average value obtained for the *Treponema*-negative samples. The *Treponema*-positive sera were purchased from SeraCare (MA, USA), the *Treponema*-negative controls were purchased from Trina Bioreactives AG (Nanikon, Switzerland).

FIG. 11 shows Table 5: Residual antigenicity of TpN47 domains C (224-351) & D (352-434) subsequent to thermal stress (72 h at 42° C.). Both domain C and D were fused to the solubility-enhancing tandem chaperone module EcSlyD-EcSlyD as described. The immunoassays were performed by using an Elecsys® 2010 analyzer. The signal dynamics (SD) are normalized relative to the average value obtained for the *Treponema*-negative samples. The *Treponema*-positive sera were purchased from SeraCare (MA, USA), the *Treponema*-negative controls were purchased from Trina Bioreactives AG (Nanikon, Switzerland).

FIG. 12 shows Table 6: Residual antigenicity of TpN47/CD (224-434) and full-length TpN47 (21-434) subsequent to thermal stress (72 h at 42° C.). Both domains CD and full-length TpN47 were fused to the solubility-enhancing tandem chaperone module EcSlyD-EcSlyD as described. The immunoassays were performed by using an Elecsys® 2010 analyzer. The signal dynamics (SD) are normalized relative to the average value obtained for the *Treponema*-negative samples. The *Treponema* positivesera were purchased from SeraCare (MA, USA), the *Treponema*-negative controls were purchased from Trina Bioreactives AG (Nanikon, Switzerland).

As further detailed in the sequence listing the following protein sequences are used within this specification:

SEQ ID NO. 1 shows full length TpN47 fused to two *E. coli* SlyD molecules: EcSlyD-EcSlyD-TpN47 (aa 21-434 TpN47 of Swiss Prot P29723 is underlined); in position 315, a cysteine has been replaced by alanine, and for purification purposes a hexa-histidine tag has been added to the C-terminal end.

```
MKVAKDLVVS LAYQVRTEDG VLVDESPVSA PLDYLHGHGS
LISGLETALE GHEVGDKFDV AVGANDAYGQ YDENLVQRVP
KDVFMGVDEL QVGMRFLAET DQGPVPVEIT AVEDDHVVVD
GNHMLAGQNL KFNVEVVAIR EATEEELAHG HVHGAHDHHH
DHDHDGGGSG GGSGGGSGGG SGGGSGGGKV AKDLVVSLAY
QVRTEDGVLV DESPVSAPLD YLHGHGSLIS GLETALEGHE
VGDKFDVAVG ANDAYGQYDE NLVQRVPKDV FMGVDELQVG
MRFLAETDQG PVPVEITAVE DDHVVVDGNH MLAGQNLKFN
VEVVAIREAT EEELAHGHVH GAHDHHHDHD HDGGGSGGGS
GGGSGGGSGG GSGGGGSSHH ETHYGYATLS YADYWAGELG
QSRDVLLAGN AEADRAGDLD AGMFDAVSRA THGHGAFRQQ
FQYAVEVLGE KVLSKQETED SRGRKKWEYE TDPSVTKMVR
ASASFQDLGE DGEIKFEAVE GAVALADRAS SFMVDSEEYK
ITNVKVHGMK FVPVAVPHEL KGIAKEKFHF VEDSRVTENT
NGLKTMLTED SFSARKVSSM ESPHDLVVDT VGTGYHSRFG
SDAEASVMLK RADGSELSHR EFIDYVMNFN TVRYDYYGDD
ASYTNLMASY GTKHSADSWW KTGRVPRISA GINYGFDRFK
GSGPGYYRLT LIANGYRDVV ADVRFLPKYE GNIDIGLKGK
VLTIGGADAE TLMDAAVDVF ADGQPKLVSD QAVSLGQNVL
SADFTPGTEY TVEVRFKEFG SVRAKVVAQL EHHHHHH
```

SEQ ID NO. 2 shows domains AB of TpN47 fused to two *E. coli* SlyD molecules: EcSlyD-EcSlyD-TpN47/AB (aa 26-223 TpN47 of Swiss Prot P29723 is underlined); for purification purposes a hexa-histidine tag has been added to the C-terminal end.

MKVAKDLVVS LAYQVRTEDG VLVDESPVSA PLDYLHGHGS
LISGLETALE GHEVGDKFDV AVGANDAYGQ YDENLVQRVP
KDVFMGVDEL QVGMRFLAET DQGPVPVEIT AVEDDHVVVD
GNHMLAGQNL KFNVEVVAIR EATEEELAHG HVHGAHDHHH
DHDHDGGGSG GGSGGGSGGG SGGGSGGGKV AKDLVVSLAY
QVRTEDGVLV DESPVSAPLD YLHGHGSLIS GLETALEGHE
VGDKFDVAVG ANDAYGQYDE NLVQRVPKDV FMGVDELQVG
MRFLAETDQG PVPVEITAVE DDHVVVDGNH MLAGQNLKFN
VEVVAIREAT EEELAHGHVH GAHDHHHDHD HDGGGSGGGS
GGGSGGGSGG GSGGGETHYG YATLSYADYW AGELGQSRDV
LLAGNAEADR AGDLDAGMFD AVSRAHGHGA FRQQFQYAVE
VLGEKVLSKQ ETEDSRGRKK WEYETDPSVT KMVRASASFQ
DLGEDGEIKF EAVEGAVALA DRASSFMVDS EEYKITNVKV
HGMKFVPVAV PHELKGIAKE KFHFVEDSRV TENTNGLKTM
LTEDSFSARK VSLEHHHHHH

SEQ ID NO. 3 shows domain B of TpN47 fused to two *E. coli* SlyD molecules: EcSlyD-EcSlyD-TpN47/B (aa 63-174 TpN47 of Swiss Prot P29723 is underlined); for purification purposes a hexa-histidine tag has been added to the C-terminal end.

MKVAKDLVVS LAYQVRTEDG VLVDESPVSA PLDYLHGHGS
LISGLETALE GHEVGDKFDV AVGANDAYGQ YDENLVQRVP
KDVFMGVDEL QVGMRFLAET DQGPVPVEIT AVEDDHVVVD
GNHMLAGQNL KFNVEVVAIR EATEEELAHG HVHGAHDHHH
DHDHDGGGSG GGSGGGSGGG SGGGSGGGKV AKDLVVSLAY
QVRTEDGVLV DESPVSAPLD YLHGHGSLIS GLETALEGHE
VGDKFDVAVG ANDAYGQYDE NLVQRVPKDV FMGVDELQVG
MRFLAETDQG PVPVEITAVE DDHVVVDGNH MLAGQNLKFN
VEVVAIREAT EEELAHGHVH GAHDHHHDHD HDGGGSGGGS
GGGSGGGSGG GSGGGDLDAG MFDAVSRATH GHGAFRQQFQ
YAVEVLGEKV LSKQETEDSR GRKKWEYETD PSVTKMVRAS
ASFQDLGEDG EIKFEAVEGA VALADRASSF MVDSEEYKIT
NVKVHGMLEH HHHHH

SEQ ID NO. 4 shows domain C of TpN47 fused to two *E. coli* SlyD molecules: EcSlyD-EcSlyD-TpN47/C (aa 224-351 TpN47 of Swiss Prot P29723 is underlined); in position 315, a cysteine has been replaced by alanine and for purification purposes a hexa-histidine tag has been added to the C-terminal end.

MKVAKDLVVS LAYQVRTEDG VLVDESPVSA PLDYLHGHGS
LISGLETALE GHEVGDKFDV AVGANDAYGQ YDENLVQRVP
KDVFMGVDEL QVGMRFLAET DQGPVPVEIT AVEDDHVVVD

-continued

GNHMLAGQNL KFNVEVVAIR EATEEELAHG HVHGAHDHHH
DHDHDGGGSG GGSGGGSGGG SGGGSGGGKV AKDLVVSLAY
QVRTEDGVLV DESPVSAPLD YLHGHGSLIS GLETALEGHE
VGDKFDVAVG ANDAYGQYDE NLVQRVPKDV FMGVDELQVG
MRFLAETDQG PVPVEITAVE DDHVVVDGNH MLAGQNLKFN
VEVVAIREAT EEELAHGHVH GAHDHHHDHD HDGGGSGGGS
GGGSGGGSGG GSGGGSMESP HDLVVDTVGT GYHSRFGSDA
EASVMLKRAD GSELSHREFI DYVMNFNTVR YDYYGDDASY
TNLMASYGTK HSADSWWKTG RVPRISAGIN YGFDRFKGSG
PGYYRLTLIA NGYRDVVADV RFLLEHHHHH H

SEQ ID NO. 5 shows domains CD of TpN47 fused to two *E. coli* SlyD molecules: EcSlyD-EcSlyD-TpN47/CD (aa 224-434 TpN47 of Swiss Prot P29723); in position 315, a cysteine has been replaced by alanine, and for purification purposes a hexa-histidine tag has been added to the C-terminal end.

MKVAKDLVVS LAYQVRTEDG VLVDESPVSA PLDYLHGHGS
LISGLETALE GHEVGDKFDV AVGANDAYGQ YDENLVQRVP
KDVFMGVDEL QVGMRFLAET DQGPVPVEIT AVEDDHVVVD
GNHMLAGQNL KFNVEVVAIR EATEEELAHG HVHGAHDHHH
DHDHDGGGSG GGSGGGSGGG SGGGSGGGKV AKDLVVSLAY
QVRTEDGVLV DESPVSAPLD YLHGHGSLIS GLETALEGHE
VGDKFDVAVG ANDAYGQYDE NLVQRVPKDV FMGVDELQVG
MRFLAETDQG PVPVEITAVE DDHVVVDGNH MLAGQNLKFN
VEVVAIREAT EEELAHGHVH GAHDHHHDHD HDGGGSGGGS
GGGSGGGSGG GSGGGSMESP HDLVVDTVGT GYHSRFGSDA
EASVMLKRAD GSELSHREFI DYVMNFNTVR YDYYGDDASY
TNLMASYGTK HSADSWWKTG RVPRISAGIN YGFDRFKGSG
PGYYRLTLIA NGYRDVVADV RFLPKYEGNI DIGLKGKVLT
IGGADAETLM DAAVDVFADG QPKLVSDQAV SLGQNVLSAD
FTPGTEYTVE VRFKEFGSVR AKVVAQLEHH HHHH

SEQ ID NO. 6 shows domain D of TpN47 fused to two *E. coli* SlyD molecules: EcSlyD-EcSlyD-TpN47/D (aa 352-434 TpN47 of Swiss Prot P29723)

MKVAKDLVVS LAYQVRTEDG VLVDESPVSA PLDYLHGHGS
LISGLETALE GHEVGDKFDV AVGANDAYGQ YDENLVQRVP
KDVFMGVDEL QVGMRFLAET DQGPVPVEIT AVEDDHVVVD
GNHMLAGQNL KFNVEVVAIR EATEEELAHG HVHGAHDHHH
DHDHDGGGSG GGSGGGSGGG SGGGSGGGKV AKDLVVSLAY
QVRTEDGVLV DESPVSAPLD YLHGHGSLIS GLETALEGHE
VGDKFDVAVG ANDAYGQYDE NLVQRVPKDV FMGVDELQVG
MRFLAETDQG PVPVEITAVE DDHVVVDGNH MLAGQNLKFN

-continued

```
VEVVAIREAT EEELAHGHVH GAHDHHHDHD HDGGGSGGGS

GGGSGGGSGG GSGGGPKYEG NIDIGLKGKV LTIGGADAET

LMDAAVDVFA DGQPKLVSDQ AVSLGQNVLS ADFTPGTEYT

VEVRFKEFGS VRAKVVAQLE HHHHHH
```

SEQ ID No. 7 shows the Linker sequence $(GGGS)_5GGG$ depicted in example 1. The glycine-rich flexible linker sequence is inserted between the two *E. coli* SlyD molecules and also between SlyD and the TpN47 antigen

```
GGGSGGGSGG GSGGGSGGGS GGG
```

SEQ ID No. 8 shows TpN47 peptide EcSlyD-TpN47/p02-1, amino acids 30-66 of the *Treponema pallidum* 47 antigen sequence according to Swiss Prot P29723:

```
GYATLSYADY WAGELGQSRD VLLAGNAEAD RAGDLDA
```

SEQ ID No. 9 shows TpN47 peptide EcSlyD-TpN47/p03-1, amino acids 106-132 of the *Treponema pallidum* 47 antigen sequence according to Swiss Prot P29723:

```
SRGRKKWEYE TDPSVTKMVR ASASFQD
```

SEQ ID No. 10 shows TpN47 peptide EcSlyD-TpN47/p04-1, amino acids 137-170 of the *Treponema pallidum* 47 antigen sequence according to Swiss Prot P29723:

```
GEIKFEAVEG AVALADRASS FMVDSEEYKI TNVK
```

SEQ ID No. 11 shows TpN47 peptide EcSlyD-TpN47/p05-1, amino acids 197-219 of the *Treponema pallidum* 47 antigen sequence according to Swiss Prot P29723:

```
EDSRVTENTN GLKTMLTEDS FSA
```

SEQ ID No. 12 shows TpN47 peptide EcSlyD-TpN47/p06-1, amino acids 225-250 of the *Treponema pallidum* 47 antigen sequence according to Swiss Prot P29723:

```
MESPHDLVVD TVGTGYHSRF GSDAEA
```

SEQ ID No. 13 shows TpN47 peptide EcSlyD-TpN47/p07-1, amino acids 273-296 of the *Treponema pallidum* 47 antigen sequence according to Swiss Prot P29723:

```
NFNTVRYDYY GDDASYTNLM ASYG
```

SEQ ID No. 14 shows TpN47 peptide EcSlyD-TpN47/p08-1, amino acids 321-362 of the *Treponema pallidum* 47 antigen sequence according to Swiss Prot P29723:

```
FDRFKGSGPG YYRLTLIANG YRDVVADVRF LPKYEGNIDI GL
```

SEQ ID No. 15 shows TpN47 peptide EcSlyD-TpN47/p09-1, amino acids 368-388 of the *Treponema pallidum* 47 antigen sequence according to Swiss Prot P29723:

```
TIGGADAETL MDAAVDVFAD G
```

SEQ ID No. 16 shows TpN47 peptide EcSlyD-TpN47/p10-1, amino acids 391-434 of the *Treponema pallidum* 47 antigen sequence according to Swiss Prot P29723:

```
KLVSDQAVSL GQNVLSADFT PGTEYTVEVR FKEFGSVRAK VVAQ
```

DETAILED DESCRIPTION OF THE INVENTION

The invention concerns soluble *Treponema pallidum* antigens, more precisely soluble variants of the *Treponema* antigen TpN47. The TpN47 antigens according to the invention lack domain C (amino acid residues 579 to 706 of SEQ ID NO.1 and are both stable and immunoreactive in an in vitro diagnostic immunoassay.

We succeeded in purifying to homogeneity full-length TpN47 from transformed prokaryotic host cells. Our initial experiments with the full-length version of TpN47 clearly revealed that this protein tends to aggregate when exposed to moderately elevated temperatures. Full-length TpN47 inevitably aggregated into a high-molecular-weight associate at temperatures above 35° C., despite the fusion of highly solubilizing tandem chaperone fusions such as EcSlyD-EcSlyD or even (the more thermostable) EcSlpA-EcSlpA to the full length antigen. In order to settle the stability problems posed by the full-length TpN47, we cloned and overproduced short TpN47 fragments as chaperone fusion proteins in *E. coli*, purified the fragments to homogeneity (as judged by Coomassie-stained SDS-PAGE gels) and assessed them for their respective antigenicity. In short, this approach was a complete failure. To our surprise, only one out of the ten fragments exhibited significant (albeit rather poor) antigenicity (see table 2/FIG. 8*a*, TpN47 30-66). The remainder of the promising short TpN47 fragments was not active at all. This finding was astonishingly at odds with the literature data given in Baughn et al., J. Immunol. (1996) 157 (2), 720-731. As a consequence, we had to search for another way to circumvent the thermally induced aggregation of the full-length TpN47.

Instead of focusing on short and presumably unstructured peptide fragments of TpN47, we sought to design conformationally folded parts of TpN47. In the Journal of Biological Chemistry (2002), 277 (4), 41857-41864, Deka et al. present the crystal structure of TpN47 and reveal the domain topology of this protein. According to this work, TpN47 consists of four domains, i.e. TpN47 comprises four autonomous folding units. However, Deka et al. are silent with regard to immunological features of the identified domains.

Surprisingly, we were able to successfully express the TpN47 domains and domain combinations AB, B, C, CD and D in an *E. coli* host. In one embodiment of the invention, the TpN47 antigens were produced in fusion with chaperone modules such as SlyD, FkpA, SlpA and Skp. All of these constructs were purified to homogeneity and assessed for their antigenicity with human anti-Syphilis sera in an automated Elecsys analyzer. The result was quite clear-cut: antigenicity was pretty high and increased in the order C<D<CD<B<<AB. Interestingly, domain C could be identified as precarious in temperature stress assays (domain C and domain combination CD strongly aggregated upon incubation at temperatures >35° C., whereas AB, B and D remained perfectly soluble). Briefly, AB, B and D were identified as TpN47 fragments with slightly reduced antigenicity but markedly improved solubility when compared to full-length TpN47. Thus, the data of our design experiments provide compelling evidence that TpN47 variants lacking the C domain are significantly improved with respect to solubility and stability.

In one embodiment of the invention, the antigen therefore comprises domain B of the *Treponema pallidum* antigen 47 (TpN47) and lacks domain C of TpN47, i.e. the invention concerns a soluble *Treponema pallidum* antigen 47 (TpN47 antigen) comprising amino acid residues 418 to 529 (domain B) of SEQ ID NO. 1 with the proviso that said antigen lacks amino acid residues 579 to 706 (domain C) of SEQ ID NO. 1 and wherein the TpN47 antigen is fused with a chaperone.

A further embodiment of the invention is a TpN47 antigen that comprises domains A and B and lacks domain C. This means that the invention covers a soluble TpN47 antigen comprising amino acid residues 381 to 578 (domain A+B) of SEQ ID NO. 1 with the proviso that said antigen lacks amino acid residues 579 to 706 (domain C) of SEQ ID NO. 1. In a further embodiment the TpN47 antigen comprises domain B or domains A+B, wherein domain D is an additional part of the TpN47 antigen. However, also in these embodiments domain C is missing. Domain D comprises amino acid residues 707 to 789 of SEQ ID NO. 1. Also in these embodiments the TpN47 antigen is fused with a chaperone.

An additional embodiment refers to a soluble *Treponema pallidum* antigen 47 (TpN47 antigen) comprising amino acid residues 418 to 529 (domain B) of SEQ ID NO. 1 with the proviso that said antigen lacks amino acid residues 579 to 706 (domain C) of SEQ ID NO. 1, additionally comprising amino acid residues 707 to 789 of SEQ ID NO. 1 (domain D).

A further embodiment relates to a soluble *Treponema pallidum* antigen 47 (TpN47 antigen) comprising amino acid residues 381 to 578 (domain A+B) of SEQ ID NO. 1 with the proviso that said antigen lacks amino acid residues 579 to 706 (domain C) of SEQ ID NO. 1, additionally comprising amino acid residues 707 to 789 of SEQ ID NO. 1 (domain D).

According to the invention the term *Treponema* is the short form of the complete term for the organism *Treponema pallidum*—the pathogen causing Syphilis—and both terms can be used interchangeably.

A "TpN47 antigen" is a protein containing a TpN47 amino acid sequence that is suitable as an antigen for use in an immunological assay. This means that the antigens according to the invention are soluble under physiological buffer conditions, for example in a phosphate buffer system at ambient temperature without addition of detergents. The antigens are also capable of binding to or being recognized and bound by antibodies specific for TpN47, like e.g. anti-TpN47 antibodies present in an isolated sample such as human sera.

According to the invention also variants of the TpN47 antigens are included. The term "variants" in this context relates to a protein or a protein fragment (i.e. a polypeptide or peptide) substantially similar to said protein. In particular, a variant may be an isoform which shows amino acid exchanges, deletions or insertions compared to the amino acid sequence of the most prevalent protein isoform. In one embodiment, such a substantially similar protein has a sequence similarity to the most prevalent isoform of the protein of at least 80%, in another embodiment at least 85% or at least 90%, in yet another embodiment at least 95%. The term "variant" also relates to a post-translationally modified protein such as a glycosylated or phosphorylated protein. According to the invention a variant classifies as a TpN47 antigen variant as long as the immunoreactivity in an in vitro diagnostic immunoassay is maintained, i.e. the variant is still able to bind and detect anti-TpN47 antibodies present in a sample. A "variant" is also a protein or antigen which has been modified for example by covalent or non-covalent attachment of a label or carrier moiety to the protein or antigen. Possible labels are radioactive, fluorescent, chemiluminescent, electrochemiluminescent, enzymes or others e.g. like digoxigenin or biotin. These labels are known to a person skilled in the art.

The antigens according to the invention can be fused to another protein. The term "fusion protein" as used in the present invention refers to a protein comprising at least one protein part corresponding to a TpN47 antigen according to the invention and at least one protein part derived from another protein that serves the role of a fusion partner.

According to another embodiment of the current invention the TpN47 antigens can be fused to chaperones. Chaperones, which are known as classical folding helpers, are proteins that assist the folding and maintenance of the structural integrity of other proteins. Examples of folding helpers are described in detail in WO 03/000877. According to the invention chaperones of the peptidyl prolyl isomerase class such as chaperones of the FKBP family can be used for fusion to the TpN47 antigen. Examples of FKBP chaperones suitable as fusion partners for TpN47 antigens are FkpA, SlyD and SlpA. A further chaperone suitable as a fusion partner for TpN47 is Skp, a periplasmic trimeric chaperone from *E. coli*, not belonging to the FKBP family. It is not always necessary to use the complete sequence of a chaperone. Functional fragments of chaperones (so-called binding-competent modules) which still possess the required abilities and functions may also be used (cf. WO 98/13496).

According to a further embodiment of the invention at least one or at least two modules of an FKBP chaperone such as e.g. *E. coli* SlyD, SlpA or FkpA are used as fusion moieties for expression of the TpN47 antigens. The chaperone Skp may be used as a fusion partner as well. The fusion of two FKBP-chaperone domains results in improved solubility of the resulting fusion polypeptide. The fusion moieties may be located N-terminally or C-terminally or at both ends (sandwich-like) of the TpN47 antigen.

The TpN47 antigens according to the invention can be generated and prepared by means of recombinant DNA techniques. Another aspect of the invention therefore is a recombinant DNA molecule encoding a TpN47 antigen and variants thereof as defined further above.

The term "recombinant DNA molecule" refers to a molecule which is made by the combination of two otherwise separated segments of sequence accomplished by the artificial manipulation of isolated segments of polynucleotides by genetic engineering techniques or by chemical synthesis. In doing so one may join together polynucleotide segments of desired functions to generate a desired combination of functions. Recombinant DNA techniques for expression of proteins in prokaryotic or lower or higher eukaryotic host cells are well known in the art. They have been described e.g. by Sambrook et al., (1989, Molecular Cloning: A Laboratory Manual)

A further subject matter of the present invention relates to a recombinant DNA molecule, encoding a *Treponema pallidum* antigen 47 (TpN47), comprising a nucleotide sequence coding for a TpN47 antigen comprising an amino acid sequence according to amino acid residues 418 to 529 (domain B) of SEQ ID NO. 1 with the proviso that said recombinant DNA molecule lacks the coding region for amino acid residues 579 to 706 (domain C) of SEQ ID NO. 1.

In another embodiment of the invention a recombinant DNA molecule encodes a TpN47 antigen comprising an amino acid sequence according to amino acid residues 381 to 578 (domain A+B) of SEQ ID NO. 1 with the proviso that said recombinant DNA molecule lacks the coding region for amino acid residues 579 to 706 (domain C) of SEQ ID NO. 1.

In a further embodiment of the invention a recombinant DNA molecule encodes a TpN47 antigen comprising an amino acid sequence according to amino acid residues 418 to 529 (domain B) or amino acid residues 381 to 578 (domain A+B) of SEQ ID NO. 1. In addition, the recombinant DNA molecule encodes an amino acid sequence comprising domain D, i.e. amino acid residues 707 to 789 of SEQ ID NO. 1. As described before, also in these embodiments the proviso applies that said recombinant DNA molecules lack the coding region for amino acid residues 579 to 706 (domain C) of SEQ ID NO. 1

The recombinant DNA molecules according to the invention may also contain sequences encoding linker peptides of 10 to 100 amino acid residues in between the TpN47 antigen and the fusion moieties and also between several fusion moieties. Such a linker sequence may for example harbor a proteolytic cleavage site.

A further aspect of the invention is an expression vector comprising operably linked a recombinant DNA molecule according to the present invention, i.e., a recombinant DNA molecule encoding a TpN47 antigen or a recombinant DNA molecule encoding a fusion protein comprising a TpN47 antigen and a peptidyl prolyl isomerase chaperone, such as an FKBP-chaperone, wherein the FKBP-chaperone is selected from FkpA, SlyD and SlpA. In an alternative embodiment the recombinant DNA molecule encodes a fusion protein comprising a TpN47 antigen and Skp. The expression vector comprising a recombinant DNA according to the present invention may be used to express the TpN47 antigen in a cell free translation system or may be used to transform a host cell for expression of the TpN47 antigen according to methods well known in the art. Another aspect of the invention therefore relates to a host cell transformed with an expression vector according to the present invention. In one embodiment of the current invention the recombinant TpN47 antigens are produced in *E. coli* cells.

Also contemplated is a method for producing a soluble, stable and immunoreactive TpN47 antigen, that can also be produced as a fusion protein containing the TpN47 antigen and a chaperone such as Skp or a peptidyl prolyl isomerase class chaperone such as an FKBP chaperone. In a further embodiment of the invention said FKBP chaperone is selected from the group consisting of SlyD, FkpA and SlpA.

This method comprises the steps of a) culturing host cells transformed with the above-described expression vector containing a gene encoding a TpN47 antigen b) expression of the gene encoding said TpN47 antigen c) purification of said TpN47 antigen.

Optionally, as an additional step d), functional solubilization needs to be carried out so that the TpN47 antigen is brought into a soluble and immunoreactive conformation by means of refolding techniques known in the art.

An additional aspect of the present invention concerns a method for the detection of anti-*Treponema* antibodies in an isolated human sample wherein a TpN47 antigen according to the invention is used as a binding partner for the antibodies. The invention thus covers a method for the detection of antibodies specific for *Treponema* in an isolated sample, said method comprising a) forming an immunoreaction admixture by admixing a body fluid sample with a TpN47 antigen according to the invention b) maintaining said immunoreaction admixture for a time period sufficient for allowing antibodies against said TpN47 antigen present in the body fluid sample to immunoreact with said TpN47 antigen to form an immunoreaction product; and c) detecting the presence and/or the concentration of any of said immunoreaction product.

In a further aspect said method is suitable for detecting *Treponema* antibodies of the IgG and the IgM subclass.

Immunoassays for detection of antibodies are well known in the art, and so are methods for carrying out such assays and practical applications and procedures. The TpN47 antigens according to the invention can be used to improve assays for the detection of anti-*Treponema* antibodies independently of the labels used and independently of the mode of detection (e.g., radioisotope assay, enzyme immunoassay, electrochemiluminescence assay, etc.) or the assay principle (e.g., test strip assay, sandwich assay, indirect test concept or homogenous assay, etc.). All biological liquids known to the expert can be used as samples for the detection of anti-*Treponema* antibodies. The samples usually used are bodily liquids like whole blood, blood sera, blood plasma, urine or saliva.

A further embodiment of the invention is an immunoassay for detecting anti-*Treponema* antibodies in an isolated sample performed according to the so-called double antigen sandwich concept (DAGS). Sometimes this assay concept is also termed double antigen bridge concept, because the two antigens are bridged by an antibody analyte. In such an assay the ability of an antibody to bind at least two different molecules of a given antigen with its two (IgG, IgA, IgE) or ten (IgM) paratopes is required and utilized.

In more detail, an immunoassay for the determination of anti-*Treponema* antibodies according to the double antigen bridge format is carried out by incubating a sample containing the anti-*Treponema* antibodies with two different TpN47 antigens, i.e. a first ("solid phase") TpN47 antigen and a second TpN47 ("detection") antigen, wherein each of the said antigens binds specifically to said anti-*Treponema* antibodies. The first antigen can be bound directly or indirectly to a solid phase and usually carries an effector group which is part of a bioaffine binding pair like, e.g., biotin and avidin. For example, if the first antigen is conjugated to biotin the solid phase is coated with either avidin or streptavidin. The second antigen carries a label. Thus an immunoreaction admixture is formed comprising the first antigen, the sample antibody and the second antigen. A solid phase to which the first antigen can be bound is added either before the addition of the sample to said antigens or after the immunoreaction admixture is formed. This immunoreaction admixture is maintained for a time period sufficient for allowing anti-*Treponema* antibodies against said TpN47 antigens in the body fluid sample to immunoreact with said TpN47 antigens to form an immunoreaction product. Next step is a separation step wherein the liquid phase is separated from the solid phase. Finally, the presence of any of said immunoreaction product is detected in the solid or liquid phase or both.

In said DAGS immunoassay the basic structures of the "solid phase antigen" and the "detection antigen" are essentially the same. It is also possible to use, in a double antigen bridge assay, similar but different TpN47 antigens, which are immunologically cross-reactive. The essential requirement for performing such assays is that the relevant epitope or the relevant epitopes are present on both antigens. According to the invention it is possible to use different fusion moieties for each TpN47 antigen (e.g. SlyD fused to TpN47 on the solid phase side and FkpA fused to TpN47 on the detection side) as such variations significantly alleviate the problem of non-specific binding and thus mitigate the risk of false-positive results.

A further embodiment of the present invention is therefore an immunoassay according to the double antigen bridge concept wherein a first TpN47 antigen or fusion protein according to the present invention, and a second TpN47 antigen or fusion protein according to the present invention are used.

The present invention further relates to the use of at least one antigen of TpN47 in a diagnostic test for the detection of anti-*Treponema* antibodies.

An additional subject matter of the invention is a reagent kit for the detection of antibodies against *Treponema*, containing, in addition to the usual test additives for immunoassays, at least one antigen of the TpN47 antigens suitable for specifically binding to *Treponema* antibodies to be determined and possibly carrying a label as well as other usual additives if necessary. In particular the reagent kit contains a TpN47 antigen comprising amino acid residues 418 to 529 (domain B) of SEQ ID NO. 1 or a TpN47 antigen comprising amino acid residues 381 to 578 (domain A+B) of SEQ ID NO. 1, with the proviso that each of said antigens lacks sequences corresponding to amino acid residues 579 to 706 (domain C) of SEQ ID NO. 1. The antigens being part of said reagent kit are fused to a chaperone.

In a further embodiment said reagent kit comprises a TpN47 antigen comprising domains B or A+B as defined before and additionally comprising domain D, i.e. amino acid residues 707 to 789 of SEQ ID NO. 1. Also in this embodiment the TpN47 antigen lacks domain C, i.e. amino acid residues 579 to 706 are not present in this TpN47 antigen.

In addition, the reagent kits defined above contain controls and standard solutions as well as reagents in one or more solutions with the common additives, buffers, salts, detergents etc. as used by the average man skilled in the art.

Another aspect is the use of the TpN47 antigens according to the invention as vaccines. The preparation of vaccines which contain an immunogenic polypeptide as active ingredient is known in the art. Such vaccines are commonly prepared as injectables, either as liquid solutions or suspensions. The active ingredient, i.e. the TpN47 antigen or its fusion protein is mixed with excipients which are pharmaceutically acceptable and compatible with the active ingredient like for example water, aqueous physiological buffers, saline, dextrose, glycerol, ethanol. The vaccines are conventionally administered parentally, by injection.

Another embodiment is a composition of at least two *Treponema pallidum* antigens comprising a TpN47 antigen according to the current invention and at least one additional *Treponema pallidum* antigen selected from the group consisting of a TpN17 antigen and a TpN15 antigen so that said composition comprises a TpN47 antigen, a TpN17 antigen or a TpN15 antigen or both TpN15 and TpN17 antigens. Yet a further embodiment is a composition of at least three *Treponema pallidum* antigens comprising a TpN47 antigen according to the current invention and both a TpN17 and a TpN15 antigen.

The invention also concerns the use of a TpN47 antigen according to the invention in an in vitro diagnostic test for the detection of anti-*Treponema pallidum* antibodies.

There are several embodiments of the present invention. For example, the present invention includes various embodiments of a soluble *Treponema pallidum* antigen 47 (TpN47 antigen), wherein certain embodiments comprise amino acid residues 418 to 529 (domain B) of SEQ ID NO. 1, lack amino acid residues 579 to 706 (domain C) of SEQ ID NO. 1, and the TpN47 antigen is fused with a chaperone. In certain embodiments, this antigen further comprises amino acid residues 707 to 789 of SEQ ID NO. 1 (domain D).

In another embodiment, the soluble *Treponema pallidum* antigen 47 (TpN47 antigen) comprises amino acid residues 381 to 578 (domain A+B) of SEQ ID NO. 1, lacks amino acid residues 579 to 706 (domain C) of SEQ ID NO. 1, and the TpN47 antigen is fused with a chaperone. In other embodiments, the soluble *Treponema pallidum* antigen 47 (TpN47 antigen) comprises amino acid residues 418 to 529 (domain B) of SEQ ID NO. 1, lacks amino acid residues 579 to 706 (domain C) of SEQ ID NO. 1, and additionally comprises amino acid residues 707 to 789 of SEQ ID NO. 1 (domain D). In yet further embodiments, the soluble *Treponema pallidum* antigen 47 (TpN47 antigen) comprises amino acid residues 381 to 578 (domain A+B) of SEQ ID NO. 1, lacks amino acid residues 579 to 706 (domain C) of SEQ ID NO. 1, and further comprises amino acid residues 4707 to 789 of SEQ ID NO. 1 (domain D).

Another aspect of the present invention is a recombinant DNA molecule encoding a *Treponema pallidum* antigen 47 (TpN47 antigen), wherein the antigen is as described above.

In other aspects, the present invention comprises an expression vector that is operably linked to a recombinant DNA molecule encoding a *Treponema pallidum* antigen 47 (TpN47 antigen) as described above, or a host cell transformed with such an expression vector.

Other aspects of the invention include methods of producing a soluble and immunoreactive *Treponema pallidum* antigen 47 (TpN47 antigen), said method comprising the steps of culturing host cells transformed with an expression vector that is operably linked to a recombinant DNA molecule encoding a TpN47 antigen as described above, expressing said TpN47 antigen and purifying said TpN47 antigen.

A further aspect of the present invention is a composition of at least two *Treponema pallidum* antigens comprising a TpN47 antigen as described above and a least one additional *Treponema pallidum* antigen selected from the group consisting of a TpN17 antigen and a TpN15 antigen.

The present invention also describes a methods for detecting antibodies specific for *Treponema pallidum* in an isolated sample. In an embodiment, said method comprises a) forming an immunoreaction admixture by admixing a body fluid sample with TpN47 antigen as described above or with a composition of at least two *Treponema pallidum* as described in the preceding composition, b) maintaining said immunoreaction admixture for a time period sufficient for allowing antibodies against said *Treponema* antigen or composition of *Treponema* antigens present in the body fluid sample to immunoreact with said *Treponema* antigen or composition of *Treponema* antigens to form an immunoreaction product; and c) detecting the presence and/or the concentration of any of said immunoreaction product.

Another aspect of the present invention is a reagent kit for the detection of anti-*Treponema pallidum* antibodies. Certain embodiments of this kit comprise at least a TpN47 antigen as described above or a composition of at least two *Treponema pallidum* antigens comprising a TpN47 antigen as described above and a least one additional *Treponema pallidum* antigen selected from the group consisting of a TpN17 antigen and a TpN15 antigen.

The examples section further illustrates the invention. In particular, the examples illustrate that we have developed and generated variants of TpN47 that are more soluble and significantly less thermolabile than the full-length TpN47 protein molecule. Both the solubility and the stability are improved. Our TpN47 variants can be abundantly overexpressed for example in *E. coli*, are easily purified and refolded via immobilized metal chelate chromatography (IMAC), exhibit satisfying stability properties and may be used to reliably detect anti-*Treponema* antibodies in human sera (in a further embodiment in combination with TpN17 and/or TpN15, two other immunodominant membrane proteins from *Treponema pallidum*). It is noteworthy that the FkpA-TpN47/AB and Skp-TpN47/AB fusion proteins form natural oligomers with epitope densities that are sufficient to detect even IgM molecules. Since we aim at developing an immunoassay for detection of total immunoglobulin (i.e. detection of both IgG and IgM), the oligomeric species FkpA-TpN47/AB and Skp-TpN47/AB may be used advantageously as specifiers on both sides of a DAGS format (e.g. FkpA-TpN47/AB-biotin and Skp-TpN47/AB-ruthenium, or vice versa).

Example 1

Cloning and Purification of TpN47 and TpN47 Chaperone Fusion Polypeptides

Cloning of Expression Cassettes

On the basis of the pET24a expression plasmid of Novagen (Madison, Wis., USA) expression cassettes encoding EcSlyD-EcSlyD-TpN47 fusion proteins were obtained essentially as described (Scholz, C. et al., J. Mol. Biol. (2005) 345, 1229-1241). The sequence of the TpN47 antigen was retrieved from the SwissProt database (SwissProt ID P29723). A synthetic gene encoding mature TpN47 aa 21-434 (the signal peptide spanning amino acid residues 1-20 was omitted) with a glycine-rich linker region fused in frame to the N-terminus was purchased from Medigenomix (Martinsried, Germany). The unique cysteine residue of TpN47 at position 315 was changed to alanine in order to prevent unwanted side-effects such as oxidation or intermolecular disulfide bridging. BamHI and XhoI restriction sites were at the 5' and the 3' ends of the TpN47-coding region, respectively. A further synthetic gene encoding two EcSlyD units (residues 1-165 according to SEQ ID NO. 1, SwissProt accession no. P0A9K9) connected via a glycine-rich linker region and encompassing part of a further linker region at the C-terminus were likewise purchased from Medigenomix. NdeI and BamHI restriction sites were at the 5' and 3' ends of this cassette, respectively. The genes and the restriction sites were designed to enable the in frame fusion of the chaperone part EcSlyD-EcSlyD and the TpN47 antigen part by simple ligation. In order to avoid inadvertent recombination processes and to increase the genetic stability of the expression cassette in the *E. coli* host, the nucleotide sequences encoding the EcSlyD units were degenerated as were the nucleotide sequences encoding the extended linker regions. i.e., different codon combinations were used to encode identical amino acid sequences.

The pET24a vector was digested with NdeI and XhoI and the cassette comprising tandem-SlyD fused in frame to the *Treponema* TpN47 fragment 21-434 (Cys 315 Ala) was inserted. Expression cassettes comprising SlyD or Skp or FkpA were constructed accordingly, as well as expression cassettes comprising target polypeptides different from full-length TpN47, notably the domains and domain combinations B (TpN47 63-174), AB (TpN47 26-223), C (TpN47 224-351), CD (TpN47 224-434) and D (TpN47 352-434). All recombinant fusion polypeptide variants contained a C-terminal hexahistidine tag to facilitate Ni-NTA-assisted purification and refolding. QuikChange (Stratagene, La Jolla, Calif., USA) and standard PCR techniques were used to generate point mutations, deletion, insertion and extension variants or restriction sites in the respective expression cassettes.

The drawing below shows a scheme of the *Treponema* TpN47 full length antigen 21-434 bearing two SlyD chaperone units fused in frame to its N-terminal end. To denote the *E. coli* origin of the SlyD fusion partner, the depicted fusion polypeptide has been named EcSlyD-EcSlyD-TpN47 (21-434).

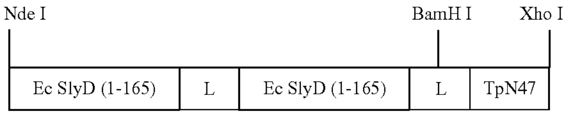

L = $(GGGS)_5$GGG-Linker

The insert of the resulting plasmid was sequenced and found to encode the desired fusion protein. The complete amino acid sequence of each individual TpN47 antigen is shown in SEQ ID NOs. 1 to 6. The amino acid sequence of the linker L is shown is SEQ ID NO. 7. Purification of fusion proteins comprising TpN47

All TpN47 fusion protein variants were purified by using virtually identical protocols. *E. coli* BL21 (DE3) cells harboring the particular pET24a expression plasmid were grown at 37° C. in LB medium plus kanamycin (30 μg/ml) to an $OD_{600}$ of 1.5, and cytosolic overexpression was induced by adding 1 mM isopropyl-β-D-thiogalactoside. Three hours after induction, cells were harvested by centrifugation (20 min at 5000 g), frozen and stored at −20° C. For cell lysis, the frozen pellet was resuspended in chilled 50 mM sodium phosphate pH 8.0, 7.0 M GdmCl, 5 mM imidazole and the suspension was stirred for 2 h on ice to complete cell lysis. After centrifugation and filtration (0.45 μm/0.2 μm), the crude lysate was applied onto a Ni-NTA column equilibrated with the lysis buffer including 5.0 mM TCEP. The subsequent washing step was tailored for the respective target protein and ranged from 5 to 15 mM imidazole (in 50 mM sodium phosphate pH 8.0, 7.0 M GdmCl, 5.0 mM TCEP). At least 10-15 volumes of the washing buffer were applied. Then, the GdmCl solution was replaced by 50 mM potassium phosphate pH 8.0, 100 mM KCl, 10 mM imidazole, 5.0 mM TCEP to induce conformational refolding of the matrix-bound protein. In order to avoid reactivation of copurifying proteases, a protease inhibitor cocktail (Complete® EDTA-free, Roche) was included in the refolding buffer. A total of 15-20 column volumes of refolding buffer were applied in an overnight reaction. Then, both TCEP and the Complete® EDTA-free inhibitor cocktail were removed by washing with 3-5 column volumes 50 mM potassium phosphate pH 8.0, 100 mM KCl, 10 mM imidazole. Subsequently, the imidazole concentration—still in 50 mM potassium phosphate pH 8.0, 100 mM KCl—was raised to 25 mM in order to remove unspecifically bound protein contaminants. The native protein was then eluted by 500 mM imidazole in the same buffer. Protein-containing fractions were assessed for purity by Tricine-SDS-PAGE and pooled. Finally, the proteins were subjected to size-exclusion-chromatography (Superdex HiLoad, Amersham Pharmacia) and the protein-containing fractions were pooled and concentrated to 10-20 mg/ml in an Amicon cell (YM10).

After the coupled purification and refolding protocol, protein yields of roughly 5-20 mg could be obtained from 1 g of *E. coli* wet cells, depending on the respective target protein.

Example 2

Spectroscopic Measurements

Protein concentration measurements were performed with an Uvikon XL double-beam spectrophotometer. The molar extinction coefficients ($\epsilon_{m280}$) were determined by using the procedure described by Pace (1995), Protein Sci. 4, 2411-2423. The molar extinction coefficients (c M280) used for the distinct Tpn47 fusion polypeptides are specified in Table 1.

TABLE 1

Protein parameters of the TpN47 fusion variants used in this study

| fusion protein | TpN47 Fragment (aa residues) | molecular weight (Da) | pI | $\epsilon_{M280}$ $M^{-1}cm^{-1}$ | $Abs_{0.1\%}$ (=1 mg/ml) |
|---|---|---|---|---|---|
| TpN47 domain variants | | | | | |
| EcSlyD-EcSlyD-TpN47 | 21-434 | 85390 | 4.9 | 63720 | 0.746 |
| EcSlyD-EcSlyD-TpN47/AB | 26-223 | 61641 | 4.8 | 33350 | 0.541 |
| EcSlyD-EcSlyD-TpN47/B | 63-174 | 52267 | 4.8 | 21890 | 0.419 |
| EcSlyD-EcSlyD-TpN47/D | 352-434 | 48561 | 4.7 | 14900 | 0.307 |
| EcSlyD-EcSlyD-TpN47/C | 224-351 | 52249 | 4.9 | 39310 | 0.725 |
| EcSlyD-EcSlyD-TpN47/CD | 224-434 | 62976 | 4.8 | 42290 | 0.672 |
| TpN47 peptide variants | | | | | |
| EcSlyD-TpN47/p02-1 | 30-66 | 24382 | 4.7 | 15930 | 0.653 |
| EcSlyD-TpN47/p03-1 | 106-132 | 23667 | 5.1 | 12950 | 0.547 |
| EcSlyD-TpN47/p04-1 | 137-170 | 24211 | 4.8 | 7450 | 0.308 |
| EcSlyD-TpN47/p05-1 | 197-219 | 23052 | 4.8 | 5960 | 0.259 |
| EcSlyD-TpN47/p06-1 | 225-250 | 23284 | 4.8 | 7450 | 0.320 |
| EcSlyD-TpN47/p07-1 | 273-296 | 23307 | 4.8 | 13410 | 0.575 |
| EcSlyD-TpN47/p08-1 | 321-362 | 25274 | 5.0 | 11920 | 0.472 |
| EcSlyD-TpN47/p09-1 | 368-388 | 22545 | 4.7 | 5960 | 0.264 |
| EcSlyD-TpN47/p10-1 | 391-434 | 25279 | 5.0 | 7450 | 0.295 |

The amino acid sequences of the TpN47 domain variants are shown in SEQ ID No. 1 to 6. The TpN47 specific sequences derived from Swiss Prot P29723 of the TpN47 peptide variants p02-1 to p10-1 are summarized in SEQ ID NOs. 8 to 16.

Example 3

Coupling of Biotin and Ruthenium Moieties to the Fusion Proteins

The lysine ε-amino groups of the fusion polypeptides were modified at protein concentrations of 10-30 mg/ml with N-hydroxy-succinimide activated biotin and ruthenium label molecules, respectively. The label/protein ratio varied from 2:1 to 5:1 (mol:mol), depending on the respective fusion protein. The reaction buffer was 150 mM potassium phosphate pH 8.0, 100 mM KCl, 1 mM EDTA. The reaction was carried out at room temperature for 15 min and stopped by adding buffered L-lysine to a final concentration of 10 mM. To avoid hydrolytic inactivation of the labels, the respective stock solutions were prepared in dried DMSO (seccosolv quality, Merck, Germany). DMSO concentrations up to 20% in the reaction buffer were well tolerated by all fusion proteins studied. After the coupling reaction, unreacted free label was removed by passing the crude protein conjugate over a gel filtration column (Superdex 200 HiLoad).

Example 4

Immunological Reactivity of the Polypeptide Fusion Proteins

The immunological reactivity (i.e. the antigenicity) of the different fusion proteins was assessed in an automated Elecsys® 2010 analyzer (Roche Diagnostics GmbH). Elecsys® is a registered trademark of the Roche group. Measurements were carried out in the double antigen sandwich format.

Signal detection in Elecsys® 2010 is based on electrochemoluminescence. The biotin-conjugate (i.e. the capture-antigen) is immobilized on the surface of a streptavidin coated magnetic bead whereas the detection-antigen bears a complexed ruthenium cation (switching between the redox states 2+ and 3+) as the signaling moiety. In the presence of a specific immunoglobulin analyte, the chromogenic ruthenium complex is bridged to the solid phase and emits light at 620 nm after excitation at a platinum electrode. The signal output is in arbitrary light units.

The recombinant *Treponema* TpN47 variants were assessed pairwise in a double antigen sandwich (DAGS) immunoassay format. For instance, an EcSlyD-EcSlyD-TpN47/AB (26-223)-biotin conjugate was assessed together with an EcSlyD-EcSlyD-TpN47/AB (26-223)-ruthenium complex conjugate at a concentration of 70 ng/ml each. As well, an EcSlyD-EcSlyD-TpN47/B (63-174)-biotin conjugate was applied together with an EcSlyD-EcSlyD-TpN47/B (63-174)-ruthenium complex conjugate at a concentration of 70 ng/ml each.

The biotin and the ruthenium conjugates of the fusion polypeptide variants of TpN47 were applied at concentrations of 70 ng/ml each. In all measurements, chemically polymerized and unlabeled EcSlyD-EcSlyD was implemented in large excess (~10 μg/ml) in the reaction buffer as an anti-interference substance to avoid immunological cross reactions via the chaperone fusion unit. Anti-*Treponema* negative human sera were used as controls.

In table 2 (FIG. 8*a-c*), the immunological activity of the TpN47 peptide fusion variants (listed in table 1) is shown. It is obvious at first glance that the antigenicity of the short TpN47 fragments is very poor when compared to the full-length TpN47 molecule. Only EcSlyD-TpN47/p02-1 (TpN47 30-66) exhibits significant antigenicity, albeit to a very low extent. From our results we conclude that some weak linear epitopes may reside in the very N-terminal part of TpN47, whereas the remainder of the TpN47 molecule does not harbor any linear epitopes detectable in our DAGS setup. This finding is strikingly at odds with literature data reporting on immunodominant short epitopes within the *Treponema* antigen TpN47 (Baughn et al., Journal of Immunology (1996) July 15; 157(2):720-31). Contrasting with these literature data, our experimental findings with short TpN47 fragments suggest that linear epitopes do play a rather subordinate role in the humoral immune response following *Treponema* infection.

As a direct consequence, we abandoned further attempts to identify linear epitopes and focused on the identification of conformational epitopes instead. In order to attain this goal, we targeted the TpN47 domains disclosed in Ranjit et al., J. Biol. Chem. (2002) 277 (44), pp 41857-41864). Different from unstructured short peptides, isolated domains (i.e. autonomous folding units) of a protein are supposed to adopt a defined conformation and thus are expected to present conformational epitopes. It was, however, totally unclear whether the isolated TpN47 domains would be able to adopt a native-like conformation when excised from the structural context of the full-length protein. Indeed, it turned out that the isolated TpN47 domains exhibit a tremendously high immunological activity when compared to the small unstructured TpN47 fragments (for results see Table 3, FIG. 9). From these data, we infer that the isolated domains are indeed able to adopt a well-ordered, native-like conformation. As judged from our immunological assessments, the antigenicity of the domain fragments increases in the order C<D<CD<B<AB<ABCD; notably, the TpN47 domain combination AB yields about 50% of the signal level of the full-length protein with anti-*Treponema*-positive human sera.

Example 5

Thermostability of TpN47 Domain Fusions as Assessed by FPLC Analysis

Having gathered compelling evidence that the TpN47 domains (i.e. the well-ordered autonomous folding units with defined conformation) exhibit significant antigenicity, we wondered whether the distinct domains would possess different stability when exposed to thermal stress. To address this question, we incubated all of our TpN47 domain fusion proteins under identical conditions and subjected them to elevated temperatures (overnight incubation in 150 mM potassium phosphate pH 8.0, 100 mM KCl, 0.5 mM EDTA at 30° C., 35° C. and 40° C., at a protein concentration of 1.3 mg/ml each). Then, we assessed all of the samples by analytical size exclusion chromatography (Superdex 200) and checked both the signal recovery (peak area under absorption curve) and the tendency to aggregate (i.e. elution of large particles in the void volume of the gel filtration column) for each TpN47 fusion protein. The results are shown in FIGS. 1-6. It turned out that the tendency to form temperature-induced aggregates significantly decreases in the order full-length-TpN47>CD>C>D, B, AB. In brief, the TpN47 domains D, B and AB are much less prone to aggregation than is full-length TpN47. Upon thermal stress, they invariably show excellent signal recovery in their elution profiles and exhibit only a negligible tendency to form associates or aggregates. Conversely, all TpN47 variants comprising domain C (i.e. full-length TpN47, C, CD) exhibit a strong tendency to aggregate even at a moderately elevated temperature such as 35° C.

Example 6

Thermostability of TpN47 Domain Fusions in Immunoassays as Assessed by Elecsys® Measurements To ascertain the thermotolerance of the distinct TpN47 fusion proteins by means of Elecsys® measurements, the EcSlyD-EcSlyD-TpN47 variants were subjected to elevated temperature conditions as follows: EcSlyD-EcSlyD-TpN47 biotin and ruthenium conjugates were incubated, separately, at 42° C. for three days. The concentration of the conjugates in this stress assay was 70 ng/ml each (~1 nM), the assay buffer was 100 mM MES pH 6.5, 300 mM NaCl, 2 mM EDTA. Subsequently, the thermally stressed samples were assessed for their residual immunological reactivity (i.e. their residual antigenicity) in an Elecsys® 2010 automated analyzer under the experimental conditions described above. Unchallenged samples (stored at 2-8° C.) of EcSlyD-EcSlyD-TpN47 were used as a reference.

The outcome of the experiments is shown in Tables 4-6 (FIGS. 10-12).

Table 4 (FIG. 10) depicts the immunological reactivity of EcSlyD-EcSlyD-TpN47/AB (26-223) and EcSlyD-EcSlyD-TpN47/B (63-174) with human anti-*Treponema* positive and anti-*Treponema* negative sera in an automated Elecsys® analyzer as described. Shown is the performance of both antigen variants before and after a harsh three-days-incubation at 42° C. Table 5 (FIG. 11) depicts the antigenicity of EcSlyD-EcSlyD-TpN47 C (224-351) and EcSlyD-EcSlyD-TpN47 D (352-434), and Table 6 (FIG. 12) displays the antigenicity of EcSlyD-EcSlyD-TpN47 CD (224-434) and of full-length TpN47 (21-434).

The outcome of the experiments clearly demonstrates the superiority of heat-stressed TpN47 domains over the full-length TpN47 protein in terms of signal recovery.

Upon thermal challenge, signal recovery of full-length TpN47 (21-434) drops to roughly 50% of the initial values, whereas the signal recovery of TpN47/B, TpN47/AB and TpN47/D amounts to ~93%, ~88% and 100% of the initial values, respectively. Thus, the signal recovery is markedly enhanced when using domains of TpN47 instead of the full-length molecule.

It is noteworthy that the C domain of TpN47 (224-351) does not exhibit any immunological activity (for results see Table 5, FIG. 11). This finding clearly contrasts with the antigenicity found for the other TpN47 domains and the domain combinations B, AB, CD and D. Seemingly, the C domain does—at least in isolation—contribute little or nothing to the astonishing antigenicity of the TpN47 protein molecule.

The CD fusion variant of TpN47 (224-434) is remarkable in that its signal recovery following 25 thermal stress amounts to roughly 70% and is clearly inferior to the other TpN47 domains and domain combinations (for results see Table 6, FIG. 12). The signal recovery of the D domain alone is very high and almost unchanged after thermal stress (see Table 5, FIG. 11).

To sum up, the TpN47 domains B, AB and D show a clearly enhanced signal recovery upon thermal challenge when compared to full-length TpN47.

According to our invention, domain C (224-351) is dispensable for immunodiagnostic purposes since it does not conspicuously contribute to TpN47 antigenicity. Furthermore, domain C, when fused to domain D, weakens the stability of the construct CD (224-434), which exhibits—exempt from full-length TpN47—the lowest signal recovery of all domains and domain combinations tested (~70%, for results see Table 6, FIG. 12).

The relative signal yield (upon thermal stress) of the distinct TpN47 domains as assessed by an automated immunoassay such as Elecsys® correlates nicely with our findings in FPLC analysis. This is remarkable all the more since both experiments have been carried out at very different concentrations: The protein concentrations in the FPLC analyses were in the medium micromolar range (15.2 μM-26.7 μM), whereas the protein concentrations in the immunological analyses were in the very low nanomolar range (0.82 nM-1.44 nM). It is expected that removal of an aggregation-inducing domain such as TpN47 domain C should yield best results (i.e. alleviate aggregation effects) under conditions of high protein concentration. Our immunological data unequivocally show that removal of domain C clearly improves both the stability and the solubility of the remainder TpN47 molecule, even under conditions of very low protein concentration. This finding enables the development of more robust immunoassay kits and constitutes a major achievement in TpN47-based serological detection of anti-*Treponema* antibodies.

Our experiments provide compelling evidence that full-length TpN47 is extremely prone to aggregation when exposed to moderately elevated temperatures above 35° C. From these observations, we infer that the use of full-length recombinant TpN47 is useful to increase the specificity and the sensitivity of any *Treponema* immunoassay, unless precautions are taken to avoid the thermally-induced loss of this aggregation-prone molecule from the assay mixture. A simple and convenient way to circumvent (or at least to mitigate) thermally-induced aggregation of TpN47 is disclosed in this patent application: it consists in simply omitting the TpN47 domain C, which apparently does not contribute directly to antigenicity and which, on top of that, seems to constitute a generally destabilizing factor within the TpN47 molecule. As soon as the TpN47 domain C is left out (as in AB, B and D), thermolability of the TpN47 protein molecule is significantly mitigated.

The invention claimed is:

1. A fusion protein comprising a soluble *Treponema pallidum* antigen 47 (TpN47 antigen), the TpN47 antigen comprising amino acid residues 418 to 529 (domain B) and lacking amino acid residues 579 to 706 (domain C) of SEQ ID NO. 1, and a chaperone.

2. The fusion protein of claim 1 wherein the soluble *Treponema pallidum* antigen 47 (TpN47 antigen) further comprises amino acid residues 707 to 789 (domain D) of SEQ ID NO. 1.

3. A fusion protein comprising a soluble *Treponema pallidum* antigen 47 (TpN47 antigen), the TpN47 antigen comprising amino acid residues 381 to 578 (domains A+B) and lacking amino acid residues 579 to 706 (domain C) of SEQ ID NO. 1, and a chaperone.

4. The fusion protein of claim 3 wherein the soluble *Treponema pallidum* antigen 47 (TpN47 antigen) further comprises amino acid residues 707 to 789 (domain D) of SEQ ID NO. 1.

5. A composition comprising at least two soluble *Treponema pallidum* antigen 47 (TpN47 antigen) antigens, the at least two soluble TpN47 antigens independently selected from the group consisting of a TpN47 antigen comprising amino acid residues 418 to 529 (domain B) and lacking amino acid residues 579 to 706 (domain C) of SEQ ID NO. 1 and a TpN47 antigen comprising amino acid residues 381 to 578 (domains A+B) and lacking amino acid residues 579 to 706 (domain C) of SEQ ID NO. 1, and at least one *Treponema pallidum* antigen selected from the group consisting of a *Treponema pallidum* antigen 17 (TpN17 antigen) and a *Treponema pallidum* antigen 15 (TpN15 antigen).

6. The composition of claim 5 wherein at least one of the at least two soluble TpN47 antigens further comprises amino acid residues 707 to 789 (domain D) of SEQ ID NO. 1.

7. The composition of claim 5 wherein at least one of the at least two soluble TpN47 antigens is part of a fusion protein, the fusion protein further comprising a chaperone.

8. A method for detecting antibodies specific for *Treponema pallidum* in an isolated sample said method comprising:

a) forming an immunoreaction admixture by admixing a body fluid sample with at least one *Treponema pallidum* antigen 47 (TpN47 antigen) selected from the group consisting of a TpN47 antigen comprising amino acid residues 418 to 529 (domain B) and lacking amino acid residues 579 to 706 (domain C) of SEQ ID NO. 1 and a TpN47 antigen variant comprising amino acid residues 381 to 578 (domains A+B) and lacking amino acid residues 579 to 706 (domain C) of SEQ ID NO. 1;

b) maintaining said immunoreaction admixture for a time period sufficient for allowing antibodies that specifically bind to said TpN47 antigen present in the body fluid sample to immunoreact with said TpN47 antigen to form an immunoreaction product; and c) detecting the presence and/or the concentration of any of said immunoreaction product.

9. The method of claim 8 wherein at least one of the TpN47 antigens further comprises amino acid residues 707 to 789 (domain D) of SEQ ID NO. 1.

10. The method of claim 8 wherein at least one of the at least two soluble TpN47 antigens is part of a fusion protein, the fusion protein further comprising a chaperone.

11. The method of claim 8 wherein at least one of the at least two soluble TpN47 antigens is included in a composition, the composition further comprising at least one *Treponema pallidum* antigen selected from the group consisting of a *Treponema pallidum* antigen 17 (TpN17 antigen) and a *Treponema pallidum* antigen 15 (TpN15 antigen).

12. A reagent kit for detecting anti-*Treponema pallidum* antibodies, comprising at least one *Treponema pallidum* antigen 47 (TpN47 antigen) selected from the group consisting of a TpN47 antigen comprising amino acid residues 418 to 529 (domain B) and lacking amino acid residues 579 to 706 (domain C) of SEQ ID NO. 1 and a TpN47 antigen comprising amino acid residues 381 to 578 (domains A+B) and lacking amino acid residues 579 to 706 (domain C) of SEQ ID NO. 1.

13. The reagent kit of claim 12 wherein the at least one of the TpN47 antigen further comprises amino acid residues 707 to 789 (domain D) of SEQ ID NO. 1.

14. The reagent kit of claim 12 wherein the at least one of the TpN47 antigen is part of a fusion protein, the fusion protein further comprising a chaperone.

15. The reagent kit of claim 12 wherein the at least one TpN47 antigen is included in a composition, the composition further comprising at least one *Treponema pallidum* antigen selected from the group consisting of a *Treponema pallidum* antigen 17 (TpN17 antigen) and a *Treponema pallidum* antigen 15 (TpN15 antigen).

* * * * *

SEQUENCE LISTING

```
<160> NUMBER OF SEQ ID NOS: 16

<210> SEQ ID NO 1
<211> LENGTH: 797
<212> TYPE: PRT
<213> ORGANISM: Artificial Sequence
<220> FEATURE:
<223> OTHER INFORMATION: Synthetic

<400> SEQUENCE: 1

Met Lys Val Ala Lys Asp Leu Val Val Ser Leu Ala Tyr Gln Val Arg
1               5                   10                  15

Thr Glu Asp Gly Val Leu Val Asp Glu Ser Pro Val Ser Ala Pro Leu
            20                  25                  30

Asp Tyr Leu His Gly His Gly Ser Leu Ile Ser Gly Leu Glu Thr Ala
        35                  40                  45

Leu Glu Gly His Glu Val Gly Asp Lys Phe Asp Val Ala Val Gly Ala
    50                  55                  60

Asn Asp Ala Tyr Gly Gln Tyr Asp Glu Asn Leu Val Gln Arg Val Pro
65                  70                  75                  80

Lys Asp Val Phe Met Gly Val Asp Glu Leu Gln Val Gly Met Arg Phe
                85                  90                  95

Leu Ala Glu Thr Asp Gln Gly Pro Val Pro Val Glu Ile Thr Ala Val
            100                 105                 110

Glu Asp Asp His Val Val Val Asp Gly Asn His Met Leu Ala Gly Gln
        115                 120                 125

Asn Leu Lys Phe Asn Val Glu Val Val Ala Ile Arg Glu Ala Thr Glu
    130                 135                 140

Glu Glu Leu Ala His Gly His Val His Gly Ala His Asp His His His
145                 150                 155                 160

Asp His Asp His Asp Gly Gly Gly Ser Gly Gly Gly Ser Gly Gly Gly
                165                 170                 175

Ser Gly Gly Gly Ser Gly Gly Gly Ser Gly Gly Gly Lys Val Ala Lys
            180                 185                 190

Asp Leu Val Val Ser Leu Ala Tyr Gln Val Arg Thr Glu Asp Gly Val
        195                 200                 205

Leu Val Asp Glu Ser Pro Val Ser Ala Pro Leu Asp Tyr Leu His Gly
    210                 215                 220

His Gly Ser Leu Ile Ser Gly Leu Glu Thr Ala Leu Glu Gly His Glu
225                 230                 235                 240

Val Gly Asp Lys Phe Asp Val Ala Val Gly Ala Asn Asp Ala Tyr Gly
                245                 250                 255

Gln Tyr Asp Glu Asn Leu Val Gln Arg Val Pro Lys Asp Val Phe Met
            260                 265                 270

Gly Val Asp Glu Leu Gln Val Gly Met Arg Phe Leu Ala Glu Thr Asp
        275                 280                 285

Gln Gly Pro Val Pro Val Glu Ile Thr Ala Val Glu Asp Asp His Val
```

-continued

```
    290                 295                 300

Val Val Asp Gly Asn His Met Leu Ala Gly Gln Asn Leu Lys Phe Asn
305                 310                 315                 320

Val Glu Val Val Ala Ile Arg Glu Ala Thr Glu Glu Glu Leu Ala His
                325                 330                 335

Gly His Val His Gly Ala His Asp His His His Asp His Asp His Asp
            340                 345                 350

Gly Gly Gly Ser Gly Gly Gly Ser Gly Gly Gly Ser Gly Gly Gly Ser
        355                 360                 365

Gly Gly Gly Ser Gly Gly Gly Gly Ser Ser His His Glu Thr His Tyr
    370                 375                 380

Gly Tyr Ala Thr Leu Ser Tyr Ala Asp Tyr Trp Ala Gly Glu Leu Gly
385                 390                 395                 400

Gln Ser Arg Asp Val Leu Leu Ala Gly Asn Ala Glu Ala Asp Arg Ala
                405                 410                 415

Gly Asp Leu Asp Ala Gly Met Phe Asp Ala Val Ser Arg Ala Thr His
            420                 425                 430

Gly His Gly Ala Phe Arg Gln Gln Phe Gln Tyr Ala Val Glu Val Leu
        435                 440                 445

Gly Glu Lys Val Leu Ser Lys Gln Glu Thr Glu Asp Ser Arg Gly Arg
    450                 455                 460

Lys Lys Trp Glu Tyr Glu Thr Asp Pro Ser Val Thr Lys Met Val Arg
465                 470                 475                 480

Ala Ser Ala Ser Phe Gln Asp Leu Gly Glu Asp Gly Glu Ile Lys Phe
                485                 490                 495

Glu Ala Val Glu Gly Ala Val Ala Leu Ala Asp Arg Ala Ser Ser Phe
            500                 505                 510

Met Val Asp Ser Glu Glu Tyr Lys Ile Thr Asn Val Lys Val His Gly
        515                 520                 525

Met Lys Phe Val Pro Val Ala Val Pro His Glu Leu Lys Gly Ile Ala
    530                 535                 540

Lys Glu Lys Phe His Phe Val Glu Asp Ser Arg Val Thr Glu Asn Thr
545                 550                 555                 560

Asn Gly Leu Lys Thr Met Leu Thr Glu Asp Ser Phe Ser Ala Arg Lys
                565                 570                 575

Val Ser Ser Met Glu Ser Pro His Asp Leu Val Val Asp Thr Val Gly
            580                 585                 590

Thr Gly Tyr His Ser Arg Phe Gly Ser Asp Ala Glu Ala Ser Val Met
        595                 600                 605

Leu Lys Arg Ala Asp Gly Ser Glu Leu Ser His Arg Glu Phe Ile Asp
    610                 615                 620

Tyr Val Met Asn Phe Asn Thr Val Arg Tyr Asp Tyr Tyr Gly Asp Asp
625                 630                 635                 640

Ala Ser Tyr Thr Asn Leu Met Ala Ser Tyr Gly Thr Lys His Ser Ala
                645                 650                 655

Asp Ser Trp Trp Lys Thr Gly Arg Val Pro Arg Ile Ser Ala Gly Ile
            660                 665                 670

Asn Tyr Gly Phe Asp Arg Phe Lys Gly Ser Gly Pro Gly Tyr Tyr Arg
        675                 680                 685

Leu Thr Leu Ile Ala Asn Gly Tyr Arg Asp Val Val Ala Asp Val Arg
    690                 695                 700

Phe Leu Pro Lys Tyr Glu Gly Asn Ile Asp Ile Gly Leu Lys Gly Lys
705                 710                 715                 720
```

```
Val Leu Thr Ile Gly Gly Ala Asp Ala Glu Thr Leu Met Asp Ala Ala
                725                 730                 735

Val Asp Val Phe Ala Asp Gly Gln Pro Lys Leu Val Ser Asp Gln Ala
            740                 745                 750

Val Ser Leu Gly Gln Asn Val Leu Ser Ala Asp Phe Thr Pro Gly Thr
        755                 760                 765

Glu Tyr Thr Val Glu Val Arg Phe Lys Glu Phe Gly Ser Val Arg Ala
    770                 775                 780

Lys Val Val Ala Gln Leu Glu His His His His His His
785                 790                 795


<210> SEQ ID NO 2
<211> LENGTH: 580
<212> TYPE: PRT
<213> ORGANISM: Artificial Sequence
<220> FEATURE:
<223> OTHER INFORMATION: Synthetic

<400> SEQUENCE: 2

Met Lys Val Ala Lys Asp Leu Val Val Ser Leu Ala Tyr Gln Val Arg
1               5                   10                  15

Thr Glu Asp Gly Val Leu Val Asp Glu Ser Pro Val Ser Ala Pro Leu
            20                  25                  30

Asp Tyr Leu His Gly His Gly Ser Leu Ile Ser Gly Leu Glu Thr Ala
        35                  40                  45

Leu Glu Gly His Glu Val Gly Asp Lys Phe Asp Val Ala Val Gly Ala
    50                  55                  60

Asn Asp Ala Tyr Gly Gln Tyr Asp Glu Asn Leu Val Gln Arg Val Pro
65                  70                  75                  80

Lys Asp Val Phe Met Gly Val Asp Glu Leu Gln Val Gly Met Arg Phe
                85                  90                  95

Leu Ala Glu Thr Asp Gln Gly Pro Val Pro Val Glu Ile Thr Ala Val
            100                 105                 110

Glu Asp Asp His Val Val Val Asp Gly Asn His Met Leu Ala Gly Gln
        115                 120                 125

Asn Leu Lys Phe Asn Val Glu Val Val Ala Ile Arg Glu Ala Thr Glu
    130                 135                 140

Glu Glu Leu Ala His Gly His Val His Gly Ala His Asp His His His
145                 150                 155                 160

Asp His Asp His Asp Gly Gly Gly Ser Gly Gly Gly Ser Gly Gly Gly
                165                 170                 175

Ser Gly Gly Gly Ser Gly Gly Gly Ser Gly Gly Gly Lys Val Ala Lys
            180                 185                 190

Asp Leu Val Val Ser Leu Ala Tyr Gln Val Arg Thr Glu Asp Gly Val
        195                 200                 205

Leu Val Asp Glu Ser Pro Val Ser Ala Pro Leu Asp Tyr Leu His Gly
    210                 215                 220

His Gly Ser Leu Ile Ser Gly Leu Glu Thr Ala Leu Glu Gly His Glu
225                 230                 235                 240

Val Gly Asp Lys Phe Asp Val Ala Val Gly Ala Asn Asp Ala Tyr Gly
                245                 250                 255

Gln Tyr Asp Glu Asn Leu Val Gln Arg Val Pro Lys Asp Val Phe Met
            260                 265                 270

Gly Val Asp Glu Leu Gln Val Gly Met Arg Phe Leu Ala Glu Thr Asp
        275                 280                 285
```

-continued

```
Gln Gly Pro Val Pro Val Glu Ile Thr Ala Val Glu Asp Asp His Val
    290                 295                 300

Val Val Asp Gly Asn His Met Leu Ala Gly Gln Asn Leu Lys Phe Asn
305                 310                 315                 320

Val Glu Val Val Ala Ile Arg Glu Ala Thr Glu Glu Glu Leu Ala His
                325                 330                 335

Gly His Val His Gly Ala His Asp His His His Asp His Asp His Asp
            340                 345                 350

Gly Gly Gly Ser Gly Gly Gly Ser Gly Gly Gly Ser Gly Gly Gly Ser
        355                 360                 365

Gly Gly Gly Ser Gly Gly Gly Glu Thr His Tyr Gly Tyr Ala Thr Leu
    370                 375                 380

Ser Tyr Ala Asp Tyr Trp Ala Gly Glu Leu Gly Gln Ser Arg Asp Val
385                 390                 395                 400

Leu Leu Ala Gly Asn Ala Glu Ala Asp Arg Ala Gly Asp Leu Asp Ala
                405                 410                 415

Gly Met Phe Asp Ala Val Ser Arg Ala His Gly His Gly Ala Phe Arg
            420                 425                 430

Gln Gln Phe Gln Tyr Ala Val Glu Val Leu Gly Glu Lys Val Leu Ser
        435                 440                 445

Lys Gln Glu Thr Glu Asp Ser Arg Gly Arg Lys Lys Trp Glu Tyr Glu
    450                 455                 460

Thr Asp Pro Ser Val Thr Lys Met Val Arg Ala Ser Ala Ser Phe Gln
465                 470                 475                 480

Asp Leu Gly Glu Asp Gly Glu Ile Lys Phe Glu Ala Val Glu Gly Ala
                485                 490                 495

Val Ala Leu Ala Asp Arg Ala Ser Ser Phe Met Val Asp Ser Glu Glu
            500                 505                 510

Tyr Lys Ile Thr Asn Val Lys Val His Gly Met Lys Phe Val Pro Val
        515                 520                 525

Ala Val Pro His Glu Leu Lys Gly Ile Ala Lys Glu Lys Phe His Phe
    530                 535                 540

Val Glu Asp Ser Arg Val Thr Glu Asn Thr Asn Gly Leu Lys Thr Met
545                 550                 555                 560

Leu Thr Glu Asp Ser Phe Ser Ala Arg Lys Val Ser Leu Glu His His
                565                 570                 575

His His His His
            580


<210> SEQ ID NO 3
<211> LENGTH: 495
<212> TYPE: PRT
<213> ORGANISM: Artificial Sequence
<220> FEATURE:
<223> OTHER INFORMATION: Synthetic

<400> SEQUENCE: 3

Met Lys Val Ala Lys Asp Leu Val Val Ser Leu Ala Tyr Gln Val Arg
1               5                   10                  15

Thr Glu Asp Gly Val Leu Val Asp Glu Ser Pro Val Ser Ala Pro Leu
            20                  25                  30

Asp Tyr Leu His Gly His Gly Ser Leu Ile Ser Gly Leu Glu Thr Ala
        35                  40                  45

Leu Glu Gly His Glu Val Gly Asp Lys Phe Asp Val Ala Val Gly Ala
    50                  55                  60
```

-continued

```
Asn Asp Ala Tyr Gly Gln Tyr Asp Glu Asn Leu Val Gln Arg Val Pro
65                  70                  75                  80

Lys Asp Val Phe Met Gly Val Asp Glu Leu Gln Val Gly Met Arg Phe
                85                  90                  95

Leu Ala Glu Thr Asp Gln Gly Pro Val Pro Val Glu Ile Thr Ala Val
            100                 105                 110

Glu Asp Asp His Val Val Val Asp Gly Asn His Met Leu Ala Gly Gln
        115                 120                 125

Asn Leu Lys Phe Asn Val Glu Val Val Ala Ile Arg Glu Ala Thr Glu
    130                 135                 140

Glu Glu Leu Ala His Gly His Val His Gly Ala His Asp His His His
145                 150                 155                 160

Asp His Asp His Asp Gly Gly Gly Ser Gly Gly Gly Ser Gly Gly Gly
                165                 170                 175

Ser Gly Gly Gly Ser Gly Gly Gly Ser Gly Gly Gly Lys Val Ala Lys
            180                 185                 190

Asp Leu Val Val Ser Leu Ala Tyr Gln Val Arg Thr Glu Asp Gly Val
        195                 200                 205

Leu Val Asp Glu Ser Pro Val Ser Ala Pro Leu Asp Tyr Leu His Gly
    210                 215                 220

His Gly Ser Leu Ile Ser Gly Leu Glu Thr Ala Leu Glu Gly His Glu
225                 230                 235                 240

Val Gly Asp Lys Phe Asp Val Ala Val Gly Ala Asn Asp Ala Tyr Gly
                245                 250                 255

Gln Tyr Asp Glu Asn Leu Val Gln Arg Val Pro Lys Asp Val Phe Met
            260                 265                 270

Gly Val Asp Glu Leu Gln Val Gly Met Arg Phe Leu Ala Glu Thr Asp
        275                 280                 285

Gln Gly Pro Val Pro Val Glu Ile Thr Ala Val Glu Asp Asp His Val
    290                 295                 300

Val Val Asp Gly Asn His Met Leu Ala Gly Gln Asn Leu Lys Phe Asn
305                 310                 315                 320

Val Glu Val Val Ala Ile Arg Glu Ala Thr Glu Glu Glu Leu Ala His
                325                 330                 335

Gly His Val His Gly Ala His Asp His His His Asp His Asp His Asp
            340                 345                 350

Gly Gly Gly Ser Gly Gly Gly Ser Gly Gly Gly Ser Gly Gly Gly Ser
        355                 360                 365

Gly Gly Gly Ser Gly Gly Gly Asp Leu Asp Ala Gly Met Phe Asp Ala
    370                 375                 380

Val Ser Arg Ala Thr His Gly His Gly Ala Phe Arg Gln Gln Phe Gln
385                 390                 395                 400

Tyr Ala Val Glu Val Leu Gly Glu Lys Val Leu Ser Lys Gln Glu Thr
                405                 410                 415

Glu Asp Ser Arg Gly Arg Lys Lys Trp Glu Tyr Glu Thr Asp Pro Ser
            420                 425                 430

Val Thr Lys Met Val Arg Ala Ser Ala Ser Phe Gln Asp Leu Gly Glu
        435                 440                 445

Asp Gly Glu Ile Lys Phe Glu Ala Val Glu Gly Ala Val Ala Leu Ala
    450                 455                 460

Asp Arg Ala Ser Ser Phe Met Val Asp Ser Glu Glu Tyr Lys Ile Thr
465                 470                 475                 480
```

-continued

```
Asn Val Lys Val His Gly Met Leu Glu His His His His His His
                485                 490                 495


<210> SEQ ID NO 4
<211> LENGTH: 511
<212> TYPE: PRT
<213> ORGANISM: Artificial Sequence
<220> FEATURE:
<223> OTHER INFORMATION: Synthetic

<400> SEQUENCE: 4

Met Lys Val Ala Lys Asp Leu Val Val Ser Leu Ala Tyr Gln Val Arg
1               5                   10                  15

Thr Glu Asp Gly Val Leu Val Asp Glu Ser Pro Val Ser Ala Pro Leu
            20                  25                  30

Asp Tyr Leu His Gly His Gly Ser Leu Ile Ser Gly Leu Glu Thr Ala
        35                  40                  45

Leu Glu Gly His Glu Val Gly Asp Lys Phe Asp Val Ala Val Gly Ala
    50                  55                  60

Asn Asp Ala Tyr Gly Gln Tyr Asp Glu Asn Leu Val Gln Arg Val Pro
65                  70                  75                  80

Lys Asp Val Phe Met Gly Val Asp Glu Leu Gln Val Gly Met Arg Phe
                85                  90                  95

Leu Ala Glu Thr Asp Gln Gly Pro Val Pro Val Glu Ile Thr Ala Val
            100                 105                 110

Glu Asp Asp His Val Val Val Asp Gly Asn His Met Leu Ala Gly Gln
        115                 120                 125

Asn Leu Lys Phe Asn Val Glu Val Val Ala Ile Arg Glu Ala Thr Glu
    130                 135                 140

Glu Glu Leu Ala His Gly His Val His Gly Ala His Asp His His His
145                 150                 155                 160

Asp His Asp His Asp Gly Gly Gly Ser Gly Gly Gly Ser Gly Gly Gly
                165                 170                 175

Ser Gly Gly Gly Ser Gly Gly Gly Ser Gly Gly Gly Lys Val Ala Lys
            180                 185                 190

Asp Leu Val Val Ser Leu Ala Tyr Gln Val Arg Thr Glu Asp Gly Val
        195                 200                 205

Leu Val Asp Glu Ser Pro Val Ser Ala Pro Leu Asp Tyr Leu His Gly
    210                 215                 220

His Gly Ser Leu Ile Ser Gly Leu Glu Thr Ala Leu Glu Gly His Glu
225                 230                 235                 240

Val Gly Asp Lys Phe Asp Val Ala Val Gly Ala Asn Asp Ala Tyr Gly
                245                 250                 255

Gln Tyr Asp Glu Asn Leu Val Gln Arg Val Pro Lys Asp Val Phe Met
            260                 265                 270

Gly Val Asp Glu Leu Gln Val Gly Met Arg Phe Leu Ala Glu Thr Asp
        275                 280                 285

Gln Gly Pro Val Pro Val Glu Ile Thr Ala Val Glu Asp Asp His Val
    290                 295                 300

Val Val Asp Gly Asn His Met Leu Ala Gly Gln Asn Leu Lys Phe Asn
305                 310                 315                 320

Val Glu Val Val Ala Ile Arg Glu Ala Thr Glu Glu Glu Leu Ala His
                325                 330                 335

Gly His Val His Gly Ala His Asp His His His Asp His Asp His Asp
            340                 345                 350
```

-continued

```
Gly Gly Gly Ser Gly Gly Gly Ser Gly Gly Gly Ser Gly Gly Gly Ser
        355                 360                 365

Gly Gly Gly Ser Gly Gly Gly Ser Met Glu Ser Pro His Asp Leu Val
    370                 375                 380

Val Asp Thr Val Gly Thr Gly Tyr His Ser Arg Phe Gly Ser Asp Ala
385                 390                 395                 400

Glu Ala Ser Val Met Leu Lys Arg Ala Asp Gly Ser Glu Leu Ser His
                405                 410                 415

Arg Glu Phe Ile Asp Tyr Val Met Asn Phe Asn Thr Val Arg Tyr Asp
            420                 425                 430

Tyr Tyr Gly Asp Asp Ala Ser Tyr Thr Asn Leu Met Ala Ser Tyr Gly
        435                 440                 445

Thr Lys His Ser Ala Asp Ser Trp Trp Lys Thr Gly Arg Val Pro Arg
    450                 455                 460

Ile Ser Ala Gly Ile Asn Tyr Gly Phe Asp Arg Phe Lys Gly Ser Gly
465                 470                 475                 480

Pro Gly Tyr Tyr Arg Leu Thr Leu Ile Ala Asn Gly Tyr Arg Asp Val
                485                 490                 495

Val Ala Asp Val Arg Phe Leu Leu Glu His His His His His His
            500                 505                 510
```

<210> SEQ ID NO 5
<211> LENGTH: 594
<212> TYPE: PRT
<213> ORGANISM: Artificial Sequence
<220> FEATURE:
<223> OTHER INFORMATION: Synthetic

<400> SEQUENCE: 5

```
Met Lys Val Ala Lys Asp Leu Val Val Ser Leu Ala Tyr Gln Val Arg
1               5                   10                  15

Thr Glu Asp Gly Val Leu Val Asp Glu Ser Pro Val Ser Ala Pro Leu
            20                  25                  30

Asp Tyr Leu His Gly His Gly Ser Leu Ile Ser Gly Leu Glu Thr Ala
        35                  40                  45

Leu Glu Gly His Glu Val Gly Asp Lys Phe Asp Val Ala Val Gly Ala
    50                  55                  60

Asn Asp Ala Tyr Gly Gln Tyr Asp Glu Asn Leu Val Gln Arg Val Pro
65                  70                  75                  80

Lys Asp Val Phe Met Gly Val Asp Glu Leu Gln Val Gly Met Arg Phe
                85                  90                  95

Leu Ala Glu Thr Asp Gln Gly Pro Val Pro Val Glu Ile Thr Ala Val
            100                 105                 110

Glu Asp Asp His Val Val Val Asp Gly Asn His Met Leu Ala Gly Gln
        115                 120                 125

Asn Leu Lys Phe Asn Val Glu Val Val Ala Ile Arg Glu Ala Thr Glu
    130                 135                 140

Glu Glu Leu Ala His Gly His Val His Gly Ala His Asp His His His
145                 150                 155                 160

Asp His Asp His Asp Gly Gly Gly Ser Gly Gly Gly Ser Gly Gly Gly
                165                 170                 175

Ser Gly Gly Gly Ser Gly Gly Gly Ser Gly Gly Gly Lys Val Ala Lys
            180                 185                 190

Asp Leu Val Val Ser Leu Ala Tyr Gln Val Arg Thr Glu Asp Gly Val
        195                 200                 205
```

-continued

```
Leu Val Asp Glu Ser Pro Val Ser Ala Pro Leu Asp Tyr Leu His Gly
    210                 215                 220

His Gly Ser Leu Ile Ser Gly Leu Glu Thr Ala Leu Glu Gly His Glu
225                 230                 235                 240

Val Gly Asp Lys Phe Asp Val Ala Val Gly Ala Asn Asp Ala Tyr Gly
                245                 250                 255

Gln Tyr Asp Glu Asn Leu Val Gln Arg Val Pro Lys Asp Val Phe Met
            260                 265                 270

Gly Val Asp Glu Leu Gln Val Gly Met Arg Phe Leu Ala Glu Thr Asp
        275                 280                 285

Gln Gly Pro Val Pro Val Glu Ile Thr Ala Val Glu Asp Asp His Val
    290                 295                 300

Val Val Asp Gly Asn His Met Leu Ala Gly Gln Asn Leu Lys Phe Asn
305                 310                 315                 320

Val Glu Val Val Ala Ile Arg Glu Ala Thr Glu Glu Glu Leu Ala His
                325                 330                 335

Gly His Val His Gly Ala His Asp His His His Asp His Asp His Asp
            340                 345                 350

Gly Gly Gly Ser Gly Gly Gly Ser Gly Gly Gly Ser Gly Gly Gly Ser
        355                 360                 365

Gly Gly Gly Ser Gly Gly Gly Ser Met Glu Ser Pro His Asp Leu Val
    370                 375                 380

Val Asp Thr Val Gly Thr Gly Tyr His Ser Arg Phe Gly Ser Asp Ala
385                 390                 395                 400

Glu Ala Ser Val Met Leu Lys Arg Ala Asp Gly Ser Glu Leu Ser His
                405                 410                 415

Arg Glu Phe Ile Asp Tyr Val Met Asn Phe Asn Thr Val Arg Tyr Asp
            420                 425                 430

Tyr Tyr Gly Asp Asp Ala Ser Tyr Thr Asn Leu Met Ala Ser Tyr Gly
        435                 440                 445

Thr Lys His Ser Ala Asp Ser Trp Trp Lys Thr Gly Arg Val Pro Arg
    450                 455                 460

Ile Ser Ala Gly Ile Asn Tyr Gly Phe Asp Arg Phe Lys Gly Ser Gly
465                 470                 475                 480

Pro Gly Tyr Tyr Arg Leu Thr Leu Ile Ala Asn Gly Tyr Arg Asp Val
                485                 490                 495

Val Ala Asp Val Arg Phe Leu Pro Lys Tyr Glu Gly Asn Ile Asp Ile
            500                 505                 510

Gly Leu Lys Gly Lys Val Leu Thr Ile Gly Gly Ala Asp Ala Glu Thr
        515                 520                 525

Leu Met Asp Ala Ala Val Asp Val Phe Ala Asp Gly Gln Pro Lys Leu
    530                 535                 540

Val Ser Asp Gln Ala Val Ser Leu Gly Gln Asn Val Leu Ser Ala Asp
545                 550                 555                 560

Phe Thr Pro Gly Thr Glu Tyr Thr Val Glu Val Arg Phe Lys Glu Phe
                565                 570                 575

Gly Ser Val Arg Ala Lys Val Val Ala Gln Leu Glu His His His His
            580                 585                 590

His His
```

<210> SEQ ID NO 6
<211> LENGTH: 466
<212> TYPE: PRT
<213> ORGANISM: Artificial Sequence
<220> FEATURE:
<223> OTHER INFORMATION: Synthetic

<400> SEQUENCE: 6

```
Met Lys Val Ala Lys Asp Leu Val Val Ser Leu Ala Tyr Gln Val Arg
1               5                   10                  15

Thr Glu Asp Gly Val Leu Val Asp Glu Ser Pro Val Ser Ala Pro Leu
            20                  25                  30

Asp Tyr Leu His Gly His Gly Ser Leu Ile Ser Gly Leu Glu Thr Ala
        35                  40                  45

Leu Glu Gly His Glu Val Gly Asp Lys Phe Asp Val Ala Val Gly Ala
    50                  55                  60

Asn Asp Ala Tyr Gly Gln Tyr Asp Glu Asn Leu Val Gln Arg Val Pro
65                  70                  75                  80

Lys Asp Val Phe Met Gly Val Asp Glu Leu Gln Val Gly Met Arg Phe
                85                  90                  95

Leu Ala Glu Thr Asp Gln Gly Pro Val Pro Val Glu Ile Thr Ala Val
            100                 105                 110

Glu Asp Asp His Val Val Val Asp Gly Asn His Met Leu Ala Gly Gln
        115                 120                 125

Asn Leu Lys Phe Asn Val Glu Val Val Ala Ile Arg Glu Ala Thr Glu
    130                 135                 140

Glu Glu Leu Ala His Gly His Val His Gly Ala His Asp His His His
145                 150                 155                 160

Asp His Asp His Asp Gly Gly Gly Ser Gly Gly Gly Ser Gly Gly Gly
                165                 170                 175

Ser Gly Gly Gly Ser Gly Gly Gly Ser Gly Gly Gly Lys Val Ala Lys
            180                 185                 190

Asp Leu Val Val Ser Leu Ala Tyr Gln Val Arg Thr Glu Asp Gly Val
        195                 200                 205

Leu Val Asp Glu Ser Pro Val Ser Ala Pro Leu Asp Tyr Leu His Gly
    210                 215                 220

His Gly Ser Leu Ile Ser Gly Leu Glu Thr Ala Leu Glu Gly His Glu
225                 230                 235                 240

Val Gly Asp Lys Phe Asp Val Ala Val Gly Ala Asn Asp Ala Tyr Gly
                245                 250                 255

Gln Tyr Asp Glu Asn Leu Val Gln Arg Val Pro Lys Asp Val Phe Met
            260                 265                 270

Gly Val Asp Glu Leu Gln Val Gly Met Arg Phe Leu Ala Glu Thr Asp
        275                 280                 285

Gln Gly Pro Val Pro Val Glu Ile Thr Ala Val Glu Asp Asp His Val
    290                 295                 300

Val Val Asp Gly Asn His Met Leu Ala Gly Gln Asn Leu Lys Phe Asn
305                 310                 315                 320

Val Glu Val Val Ala Ile Arg Glu Ala Thr Glu Glu Glu Leu Ala His
                325                 330                 335

Gly His Val His Gly Ala His Asp His His His Asp His Asp His Asp
            340                 345                 350

Gly Gly Gly Ser Gly Gly Gly Ser Gly Gly Gly Ser Gly Gly Gly Ser
        355                 360                 365

Gly Gly Gly Ser Gly Gly Gly Pro Lys Tyr Glu Gly Asn Ile Asp Ile
    370                 375                 380

Gly Leu Lys Gly Lys Val Leu Thr Ile Gly Gly Ala Asp Ala Glu Thr
385                 390                 395                 400
```

Leu Met Asp Ala Ala Val Asp Val Phe Ala Asp Gly Gln Pro Lys Leu
405 410 415

Val Ser Asp Gln Ala Val Ser Leu Gly Gln Asn Val Leu Ser Ala Asp
420 425 430

Phe Thr Pro Gly Thr Glu Tyr Thr Val Glu Val Arg Phe Lys Glu Phe
435 440 445

Gly Ser Val Arg Ala Lys Val Val Ala Gln Leu Glu His His His His
450 455 460

His His
465

<210> SEQ ID NO 7
<211> LENGTH: 23
<212> TYPE: PRT
<213> ORGANISM: Artificial Sequence
<220> FEATURE:
<223> OTHER INFORMATION: Synthetic

<400> SEQUENCE: 7

Gly Gly Gly Ser Gly Gly Gly Ser Gly Gly Gly Ser Gly Gly Gly Ser
1 5 10 15

Gly Gly Gly Ser Gly Gly Gly
20

<210> SEQ ID NO 8
<211> LENGTH: 37
<212> TYPE: PRT
<213> ORGANISM: Artificial Sequence
<220> FEATURE:
<223> OTHER INFORMATION: Synthetic

<400> SEQUENCE: 8

Gly Tyr Ala Thr Leu Ser Tyr Ala Asp Tyr Trp Ala Gly Glu Leu Gly
1 5 10 15

Gln Ser Arg Asp Val Leu Leu Ala Gly Asn Ala Glu Ala Asp Arg Ala
20 25 30

Gly Asp Leu Asp Ala
35

<210> SEQ ID NO 9
<211> LENGTH: 27
<212> TYPE: PRT
<213> ORGANISM: Artificial Sequence
<220> FEATURE:
<223> OTHER INFORMATION: Synthetic

<400> SEQUENCE: 9

Ser Arg Gly Arg Lys Lys Trp Glu Tyr Glu Thr Asp Pro Ser Val Thr
1 5 10 15

Lys Met Val Arg Ala Ser Ala Ser Phe Gln Asp
20 25

<210> SEQ ID NO 10
<211> LENGTH: 34
<212> TYPE: PRT
<213> ORGANISM: Artificial Sequence
<220> FEATURE:
<223> OTHER INFORMATION: Synthetic

<400> SEQUENCE: 10

Gly Glu Ile Lys Phe Glu Ala Val Glu Gly Ala Val Ala Leu Ala Asp
1 5 10 15

Arg Ala Ser Ser Phe Met Val Asp Ser Glu Glu Tyr Lys Ile Thr Asn
20 25 30

Val Lys

<210> SEQ ID NO 11
<211> LENGTH: 23
<212> TYPE: PRT
<213> ORGANISM: Artificial Sequence
<220> FEATURE:
<223> OTHER INFORMATION: Synthetic

<400> SEQUENCE: 11

Glu Asp Ser Arg Val Thr Glu Asn Thr Asn Gly Leu Lys Thr Met Leu
1 5 10 15

Thr Glu Asp Ser Phe Ser Ala
20

<210> SEQ ID NO 12
<211> LENGTH: 26
<212> TYPE: PRT
<213> ORGANISM: Artificial Sequence
<220> FEATURE:
<223> OTHER INFORMATION: Synthetic

<400> SEQUENCE: 12

Met Glu Ser Pro His Asp Leu Val Val Asp Thr Val Gly Thr Gly Tyr
1 5 10 15

His Ser Arg Phe Gly Ser Asp Ala Glu Ala
20 25

<210> SEQ ID NO 13
<211> LENGTH: 24
<212> TYPE: PRT
<213> ORGANISM: Artificial Sequence
<220> FEATURE:
<223> OTHER INFORMATION: Synthetic

<400> SEQUENCE: 13

Asn Phe Asn Thr Val Arg Tyr Asp Tyr Tyr Gly Asp Asp Ala Ser Tyr
1 5 10 15

Thr Asn Leu Met Ala Ser Tyr Gly
20

<210> SEQ ID NO 14
<211> LENGTH: 42
<212> TYPE: PRT
<213> ORGANISM: Artificial Sequence
<220> FEATURE:
<223> OTHER INFORMATION: Synthetic

<400> SEQUENCE: 14

Phe Asp Arg Phe Lys Gly Ser Gly Pro Gly Tyr Tyr Arg Leu Thr Leu
1 5 10 15

Ile Ala Asn Gly Tyr Arg Asp Val Val Ala Asp Val Arg Phe Leu Pro
20 25 30

Lys Tyr Glu Gly Asn Ile Asp Ile Gly Leu
35 40

<210> SEQ ID NO 15
<211> LENGTH: 21
<212> TYPE: PRT
<213> ORGANISM: Artificial Sequence
<220> FEATURE:

-continued

```
<223> OTHER INFORMATION: Synthetic

<400> SEQUENCE: 15

Thr Ile Gly Gly Ala Asp Ala Glu Thr Leu Met Asp Ala Ala Val Asp
1               5                   10                  15

Val Phe Ala Asp Gly
            20


<210> SEQ ID NO 16
<211> LENGTH: 44
<212> TYPE: PRT
<213> ORGANISM: Artificial Sequence
<220> FEATURE:
<223> OTHER INFORMATION: Synthetic

<400> SEQUENCE: 16

Lys Leu Val Ser Asp Gln Ala Val Ser Leu Gly Gln Asn Val Leu Ser
1               5                   10                  15

Ala Asp Phe Thr Pro Gly Thr Glu Tyr Thr Val Glu Val Arg Phe Lys
            20                  25                  30

Glu Phe Gly Ser Val Arg Ala Lys Val Val Ala Gln
        35                  40
```